United States Patent
Fenstermaker et al.

(10) Patent No.: US 10,738,129 B2
(45) Date of Patent: *Aug. 11, 2020

(54) ANTI-SURVIVIN ANTIBODIES FOR CANCER THERAPY

(71) Applicant: Health Research, Inc., Buffalo, NY (US)

(72) Inventors: Robert A. Fenstermaker, Amherst, NY (US); Michael J. Ciesielski, Orchard Park, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/233,375

(22) Filed: Dec. 27, 2018

(65) Prior Publication Data

US 2019/0119398 A1    Apr. 25, 2019

Related U.S. Application Data

(63) Continuation of application No. 15/257,324, filed on Sep. 6, 2016, now Pat. No. 10,167,340.

(60) Provisional application No. 62/214,242, filed on Sep. 4, 2015.

(51) Int. Cl.
| | |
|---|---|
| C07K 16/18 | (2006.01) |
| C07K 16/30 | (2006.01) |
| C12N 5/10 | (2006.01) |
| C12N 5/16 | (2006.01) |
| C12N 15/113 | (2010.01) |
| C12N 15/62 | (2006.01) |
| A61K 35/17 | (2015.01) |
| C12N 5/0783 | (2010.01) |
| A61K 39/00 | (2006.01) |

(52) U.S. Cl.
CPC .............. *C07K 16/30* (2013.01); *C07K 16/18* (2013.01); *A61K 35/17* (2013.01); *A61K 2039/505* (2013.01); *C07K 2317/14* (2013.01); *C07K 2317/34* (2013.01); *C07K 2317/56* (2013.01); *C07K 2317/92* (2013.01); *C12N 5/0636* (2013.01); *C12N 5/16* (2013.01); *C12N 15/1136* (2013.01); *C12N 15/62* (2013.01); *C12N 2510/00* (2013.01)

(58) Field of Classification Search
CPC .... C07K 16/18; C07K 16/30; C07K 2317/14; C07K 2317/34; C07K 2317/56; C07K 2317/92; C12N 5/16; C12N 15/62; A61K 35/17
See application file for complete search history.

(56) References Cited

U.S. PATENT DOCUMENTS

| | | | |
|---|---|---|---|
| 7,943,138 B2 | 5/2011 | Ciesielski et al. | |
| 8,580,269 B2 | 11/2013 | Ciesielski et al. | |
| 2008/0213277 A1 | 9/2008 | Sasu et al. | |
| 2009/0286312 A1 | 11/2009 | Dong et al. | |
| 2011/0136743 A1 | 6/2011 | Altieri | |
| 2012/0082667 A1* | 4/2012 | Yokoseki | C07K 16/18 424/133.1 |
| 2014/0234350 A1 | 8/2014 | Yu et al. | |

FOREIGN PATENT DOCUMENTS

WO    2009012460 A1    1/2009

OTHER PUBLICATIONS

Overbeek, "Factors affecting transgenic animal production," Transgenic animal technology, 1994, pp. 96-98.*
Wall, Theriogenology, 1996, vol. 45, pp. 57-68.*
Houdebine, J. Biotech. 1994, vol. 34, pp. 269-287.*
Kappell, Current Opinions in Biotechnology, 1992, vol. 3, pp. 548-553.*
Liu et al., Methods Mol Biol. 2013, 1027: 1-17.*
Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Ramos et al., Expert Opin. Biol. Ther., 2011, 11(7): 855-873.*
Fortugno et al., Survivin exists in immunochemically distinct subcellular pools and is involved in spindle microtubule function, J. Cell Science, Feb. 2002, vol. 115, No. 3, pp. 575-585.
Zhang et al., Silencing survivin expression inhibits the tumor growth of non-small-cell lung cancer cells in vitro and in vivo, Molecular Medicine Reports, vol. 11, No. 1, pp. 639-644 Oct. 21, 2014.
Fenstermaker et al., Survivin Monoclonal Antibodies Detect Survivin Cell Surface Expression and Inhibit Tumor Growth In Vivo, Clinical Cancer Research, vol. 24, No. 11, pp. 2642-2652 Mar. 14, 2018.

* cited by examiner

Primary Examiner — Hong Sang
(74) Attorney, Agent, or Firm — Hodgson Russ LLP

(57) ABSTRACT

Provided are survivin specific antibodies, nucleic acids encoding the antibodies and methods for treating tumors comprising survivin-expressing cells by administration of the antibodies. The antibody compositions were found to be effective in inhibiting the growth of tumors.

5 Claims, 12 Drawing Sheets

Specification includes a Sequence Listing.

SEQUENCE LISTING

<160> NUMBER OF SEQ ID NOS: 27

<210> SEQ ID NO 1
<211> LENGTH: 23
<212> TYPE: PRT

```
<213> ORGANISM: human

<400> SEQUENCE: 1

Glu Asn Glu Pro Asp Leu Ala Gln Cys Phe Phe Cys Phe Lys Glu Leu
1               5                   10                  15

Glu Gly Trp Glu Pro Asp Asp
            20

<210> SEQ ID NO 2
<211> LENGTH: 23
<212> TYPE: PRT
<213> ORGANISM: artificial sequence
<220> FEATURE:
<223> OTHER INFORMATION: Mutant protein

<400> SEQUENCE: 2

Glu Asn Glu Pro Asp Leu Ala Gln Met Phe Phe Cys Phe Lys Glu Leu
1               5                   10                  15

Glu Gly Trp Glu Pro Asp Asp
            20

<210> SEQ ID NO 3
<211> LENGTH: 6
<212> TYPE: PRT
<213> ORGANISM: artificial sequence
<220> FEATURE:
<223> OTHER INFORMATION: Protein fragment

<400> SEQUENCE: 3

Gln Met Phe Phe Cys Phe
1               5

<210> SEQ ID NO 4
<211> LENGTH: 15
<212> TYPE: PRT
<213> ORGANISM: artificial sequence
<220> FEATURE:
<223> OTHER INFORMATION: Protein fragment

<400> SEQUENCE: 4

Asp Leu Ala Gln Met Phe Phe Cys Phe Lys Glu Leu Glu Gly Trp
1               5                   10                  15

<210> SEQ ID NO 5
<211> LENGTH: 10
<212> TYPE: PRT
<213> ORGANISM: artificial sequence
<220> FEATURE:
<223> OTHER INFORMATION: Protein fragment

<400> SEQUENCE: 5

Ala Gln Met Phe Phe Cys Phe Lys Glu Leu
1               5                   10

<210> SEQ ID NO 6
<211> LENGTH: 9
<212> TYPE: PRT
<213> ORGANISM: artificial sequence
<220> FEATURE:
<223> OTHER INFORMATION: Protein fragment

<400> SEQUENCE: 6

Gln Met Phe Phe Cys Phe Lys Glu Leu
1               5
```

```
<210> SEQ ID NO 7
<211> LENGTH: 5
<212> TYPE: PRT
<213> ORGANISM: artificial sequence
<220> FEATURE:
<223> OTHER INFORMATION: Antibody sequence

<400> SEQUENCE: 7

Thr Tyr Gly Met Ser
1               5

<210> SEQ ID NO 8
<211> LENGTH: 17
<212> TYPE: PRT
<213> ORGANISM: artificial sequence
<220> FEATURE:
<223> OTHER INFORMATION: Antibody sequence

<400> SEQUENCE: 8

Trp Ile Asn Pro Tyr Ser Gly Val Pro Thr Tyr Ala Val Asp Phe Lys
1               5                   10                  15

Gly

<210> SEQ ID NO 9
<211> LENGTH: 9
<212> TYPE: PRT
<213> ORGANISM: artificial sequence
<220> FEATURE:
<223> OTHER INFORMATION: Antibody sequence

<400> SEQUENCE: 9

Gly Gly Arg Arg Gly Asp Phe Gly Tyr
1               5

<210> SEQ ID NO 10
<211> LENGTH: 10
<212> TYPE: PRT
<213> ORGANISM: artificial sequence
<220> FEATURE:
<223> OTHER INFORMATION: Antibody sequence

<400> SEQUENCE: 10

Ser Ala Ser Ser Ser Ile Ser Tyr Met His
1               5                   10

<210> SEQ ID NO 11
<211> LENGTH: 7
<212> TYPE: PRT
<213> ORGANISM: artificial sequence
<220> FEATURE:
<223> OTHER INFORMATION: Antibody sequence

<400> SEQUENCE: 11

Asp Thr Ser Lys Leu Ala Ser
1               5

<210> SEQ ID NO 12
<211> LENGTH: 8
<212> TYPE: PRT
<213> ORGANISM: artificial sequence
<220> FEATURE:
<223> OTHER INFORMATION: Antibody sequence

<400> SEQUENCE: 12

His Gln Arg Ser Ser His His Thr
1               5
```

```
<210> SEQ ID NO 13
<211> LENGTH: 5
<212> TYPE: PRT
<213> ORGANISM: artificial sequence
<220> FEATURE:
<223> OTHER INFORMATION: Antibody sequence

<400> SEQUENCE: 13

Ser Tyr Gly Met Ser
1               5

<210> SEQ ID NO 14
<211> LENGTH: 17
<212> TYPE: PRT
<213> ORGANISM: artificial sequence
<220> FEATURE:
<223> OTHER INFORMATION: Antibody sequence

<400> SEQUENCE: 14

Thr Ile Ser Ser Gly Gly Ser His Thr Tyr Tyr Pro Asp Ser Val Arg
1               5                   10                  15

Gly

<210> SEQ ID NO 15
<211> LENGTH: 14
<212> TYPE: PRT
<213> ORGANISM: artificial sequence
<220> FEATURE:
<223> OTHER INFORMATION: Antibody sequence

<400> SEQUENCE: 15

His Pro Ile Tyr Tyr Tyr Ile Ser Ser Tyr Ala Met Asp Tyr
1               5                   10

<210> SEQ ID NO 16
<211> LENGTH: 16
<212> TYPE: PRT
<213> ORGANISM: artificial sequence
<220> FEATURE:
<223> OTHER INFORMATION: Antibody sequence

<400> SEQUENCE: 16

Arg Ser Ser Gln Ser Leu Val His Ser Thr Gly Asn Thr Tyr Leu His
1               5                   10                  15

<210> SEQ ID NO 17
<211> LENGTH: 7
<212> TYPE: PRT
<213> ORGANISM: artificial sequence
<220> FEATURE:
<223> OTHER INFORMATION: Antibody sequence

<400> SEQUENCE: 17

Lys Val Ser Asn Arg Phe Ser
1               5

<210> SEQ ID NO 18
<211> LENGTH: 9
<212> TYPE: PRT
<213> ORGANISM: artificial sequence
<220> FEATURE:
<223> OTHER INFORMATION: Antibody sequence

<400> SEQUENCE: 18

Ser Gln Ser Thr His Val Pro Pro Thr
1               5
```

<210> SEQ ID NO 19
<211> LENGTH: 137
<212> TYPE: PRT
<213> ORGANISM: artificial sequence
<220> FEATURE:
<223> OTHER INFORMATION: Antibody sequence

<400> SEQUENCE: 19

```
Met Gly Trp Leu Trp Asn Leu Leu Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
            35                  40                  45

Thr Thr Tyr Gly Met Ser Trp Val Lys Gln Ala Pro Gly Arg Gly Leu
    50                  55                  60

Lys Trp Met Gly Trp Ile Asn Pro Tyr Ser Gly Val Pro Thr Tyr Ala
65                  70                  75                  80

Val Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Gly Gly Arg Arg Gly Asp Phe Gly Tyr Trp Gly
        115                 120                 125

Gln Gly Thr Thr Leu Thr Val Ser Ser
        130                 135
```

<210> SEQ ID NO 20
<211> LENGTH: 127
<212> TYPE: PRT
<213> ORGANISM: artificial sequence
<220> FEATURE:
<223> OTHER INFORMATION: Antibody sequence

<400> SEQUENCE: 20

```
Met Asp Phe Gln Val Gln Ile Phe Ser Phe Leu Leu Ile Ser Ala Ser
1               5                   10                  15

Val Ile Leu Ser Ser Gly Gln Ile Gly Leu Thr Gln Ser Pro Ala Ile
            20                  25                  30

Met Ser Ala Ser Pro Gly Glu Lys Val Thr Met Thr Cys Ser Ala Ser
            35                  40                  45

Ser Ser Ile Ser Tyr Met His Trp Tyr Gln Gln Lys Pro Gly Thr Ser
    50                  55                  60

Pro Lys Thr Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Arg
            100                 105                 110

Ser Ser His His Thr Phe Gly Gly Gly Thr Lys Leu Glu Ile Lys
        115                 120                 125
```

<210> SEQ ID NO 21
<211> LENGTH: 142
<212> TYPE: PRT
<213> ORGANISM: artificial sequence
<220> FEATURE:
<223> OTHER INFORMATION: Antibody sequence

<400> SEQUENCE: 21

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Leu Thr Pro Asp Lys Arg Leu
    50                  55                  60

Glu Trp Val Ala Thr Ile Ser Ser Gly Gly Ser His Thr Tyr Tyr Pro
65                  70                  75                  80

Asp Ser Val Arg Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Pro Tyr Tyr Ile Ser Ser Tyr Ala
        115                 120                 125

Met Asp Tyr Trp Gly Gln Gly Thr Ser Val Thr Val Ser Ser
    130                 135                 140

<210> SEQ ID NO 22
<211> LENGTH: 131
<212> TYPE: PRT
<213> ORGANISM: artificial sequence
<220> FEATURE:
<223> OTHER INFORMATION: Antibody sequence

<400> SEQUENCE: 22

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Thr Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Gly Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Pro Thr Phe Gly Gly Gly Thr Lys Leu
        115                 120                 125

Glu Ile Lys
    130

<210> SEQ ID NO 23
<211> LENGTH: 411
<212> TYPE: DNA
<213> ORGANISM: artificial sequence
<220> FEATURE:
<223> OTHER INFORMATION: Antibody gene sequence

<400> SEQUENCE: 23
atgggttggc tgtggaactt gctattcctg atggcagctg cccaaagtgc ccaagcacag    60

```
atccagttgg tacaatctgg acctgagctg aagaagcctg agagacagt caagatctcc      120 tgcaaggctt ctgggtatac cttcacaacc tatggaatga ctgggtgaa acaggctcca      180 ggaaggggtt taaagtggat gggctggata accccctact ctggagtgcc aacatatgct    240
gttgacttca agggacggtt tgccttctct ttggaaacct ctgccagcac tgcctatttg    300
cagatcaaca acctcaaaaa tgaggacacg gctacatatt tctgtgcaag aggagggcgg    360 agggggggact ttggctactg gggccaaggc accactctca cagtctcctc a            411
```

<210> SEQ ID NO 24
<211> LENGTH: 381
<212> TYPE: DNA
<213> ORGANISM: artificial sequence
<220> FEATURE:
<223> OTHER INFORMATION: Antibody gene sequence

<400> SEQUENCE: 24

```
atggattttc aggtgcagat tttcagcttc ctgctaatca gtgcctcagt catactgtcc    60
agcggacaaa ttggtctcac ccagtctcca gcaatcatgt ctgcatctcc aggggagaag    120
gtcaccatga cctgcagtgc cagctcaagt ataagttaca tgcattggta ccagcagaag    180
ccaggcacct cccccaaaac atggatttat gacacatcca aactggcttc tggagtccct    240
gctcgcttca gtggcagtgg gtctgggacc tcttattctc tcacaatcag cagcatggag    300
gctgaagatg ctgccactta ttactgccat cagcggagta gtcaccacac gttcggaggg    360
gggaccaagc tggaaataaa a                                              381
```

<210> SEQ ID NO 25
<211> LENGTH: 426
<212> TYPE: DNA
<213> ORGANISM: artificial sequence
<220> FEATURE:
<223> OTHER INFORMATION: Antibody gene sequence

<400> SEQUENCE: 25

```
atgaacttcg ggctcagctt gattttcctt gcccttattt taaaggtgt ccagtgtgag      60 gtgcagctgg tggagtctgg gggagactta gtgaagcctg agggtccct gaaactctcc    120 tgtgcagcct ctggattcac tttcagtagc tatggcatgt cttgggttcg cctgactcca    180
gacaagaggc tggagtgggt cgcaaccatt agcagtggtg gtagtcacac ctactatcca    240
gacagtgtga gggggcgatt caccatctcc agagacaatg ccaagaacac cctgtacctg    300
caaatgagca gtctgaagtc tgaggacaca gccatgtatt actgtgcaag acacccaatt    360
tattactaca ttagtagcta tgctatggac tactgggtc aaggaacctc agtcaccgtc    420
tcctca                                                                426
```

<210> SEQ ID NO 26
<211> LENGTH: 393
<212> TYPE: DNA
<213> ORGANISM: artificial sequence
<220> FEATURE:
<223> OTHER INFORMATION: antibody gene sequence

<400> SEQUENCE: 26

```
atgaagttgc ctgttaggct gttggtgctg atgttctgga ttcctgcttc cagcagtgat    60
gttgtgatga cccaaactcc actctccctg cctgtcagtc ttggagatca agcctccatc    120
tcttgcagat ctagtcagag ccttgtacac agtactggaa acacctattt acattggtac    180
ctgcagaagc caggccagtc tccaaagctc ctgatctaca agtttccaa ccgatttct    240
```

```
ggggtcccag acaggttcgg tggcagtgga tcagggacag atttcacact caagatcagc    300
agagtggagg ctgaggatct gggagtttat ttctgctctc aaagtacaca tgttcctccg    360
acgttcggtg gaggcaccaa gctggaaatc aaa                                  393

<210> SEQ ID NO 27
<211> LENGTH: 15
<212> TYPE: PRT
<213> ORGANISM: human

<400> SEQUENCE: 27

Asp Leu Ala Gln Cys Phe Phe Cys Phe Lys Glu Leu Glu Gly Trp
1               5                   10                  15
```

ANTI-SURVIVIN ANTIBODIES FOR CANCER THERAPY

CROSS-REFERENCE TO RELATED APPLICATIONS

This application is a continuation of U.S. patent application Ser. No. 15/257,324, filed on Sep. 6, 2016, which claims priority to U.S. Provisional patent application No. 62/214,242, filed on Sep. 4, 2015, the disclosures of which are incorporated herein by reference.

BACKGROUND OF THE DISCLOSURE

Survivin is an intracellular protein that belongs to a family of apoptosis inhibitors. Survivin acts in concert with the mitotic spindle apparatus to regulate cell division. It is expressed in certain cells during the G2/M phase of the cell cycle and associates with the spindle microtubule organizing center during this phase of cell cycle progression. Survivin functions in critical roles at a number of different cellular loci to regulate the cell cycle and to inhibit apoptotic cell death. It is frequently expressed by cancer cells of many different types, but uncommonly by normal adult tissues. Survivin peptide sequences have been used to develop vaccination strategies. While the survival of patients with some cancers has improved, challenges remain, particularly for those with advanced disease at diagnosis. As such, there continues to be a need to develop additional strategies to combat cancer.

SUMMARY OF THE DISCLOSURE

The present disclosure provides compositions and methods for treatment of tumors that comprise survivin-expressing cells. The disclosure provides isolated antibodies, including monoclonal and polyclonal antibodies and fragments and variants thereof, compositions comprising the antibodies, nucleic acid molecules encoding the antibodies or portions thereof or variants thereof, vectors comprising the nucleic acid molecules, cells comprising the antibodies and/or nuclei acid molecules, kits comprising one or more antibodies or nucleic acid molecules, and methods of using the antibodies or nucleic acid molecules or cells comprising the antibodies or nucleic acid molecules to inhibit the growth of tumors.

In one aspect, the disclosure provides an isolated antibody, which may be a polyclonal or a monoclonal antibody (mAb), which is specifically reactive against one or more epitopes of survivin. The antibody may be generated in response to administration of a peptide of survivin or a modification thereof. For example, an antibody can be generated in response to a peptide, which may be 9 to 23 amino acids long and comprises the core sequence QMFFCF (SEQ ID NO:3).

An antibody of this disclosure can be a monoclonal antibody comprising a heavy chain variable region (VH) comprising a complementarity-determining region (CDR) 1 having a sequence set forth in SEQ ID NO:7, a CDR2 having a sequence set forth in SEQ ID NO:8 and a CDR3 having a sequence set forth in SEQ ID NO:9, and a light chain variable region (VL) comprising a CDR1 having a sequence set forth in SEQ ID NO:10, a CDR2 having a sequence set forth in SEQ ID NO:11 and a CDR3 having a sequence set forth in SEQ ID NO:12; or a monoclonal antibody comprising a VH comprising a CDR1 having a sequence set forth in SEQ ID NO:13, a CDR2 having a sequence set forth in SEQ ID NO:14 and a CDR3 having a sequence set forth in SEQ ID NO: 5, and a VL comprising a CDR1 having a sequence set forth in SEQ ID NO:16, a CDR2 having a sequence set forth in SEQ ID NO:17 and a CDR3 having a sequence set forth in SEQ ID NO:18.

The antibodies of the present disclosure may be chimeric, human, or humanized antibodies. In a chimeric or humanized antibodies, some portions of the heavy and/or light chains may be identical or homologous to sequences from one species while other portions may be identical or homologous to sequences from a different species. For example, murine monoclonal antibodies may be isolated or generated and then portions of these antibodies (or sequence information derived therefrom) used for generating chimeric or humanized antibodies. For example, mice may be immunized with one or more survivin peptides and then ascites fluid samples can be collected. The samples can be screened and selected to develop a panel of monoclonal antibodies and corresponding hybridoma cell lines. Portions or sequences from the monoclonal antibodies can then be used to generate chimeric or humanized antibodies. An antibody of the present disclosure can also be an antibody fragment, a single chain, a bispecific or multispecific antibody.

The disclosure provides nucleic acid molecules comprising sequences encoding portions or all of the antibodies (including mAbs) sequences. The disclosure also provides cells comprising the nucleic acid molecules.

This disclosure provides a method of treating a tumor in an individual in need of treatment comprising administering to the individual a composition comprising one or more antibodies that are specific for survivin, such as, for example, human survivin.

DETAILED DESCRIPTION OF THE DISCLOSURE

Figure 1:
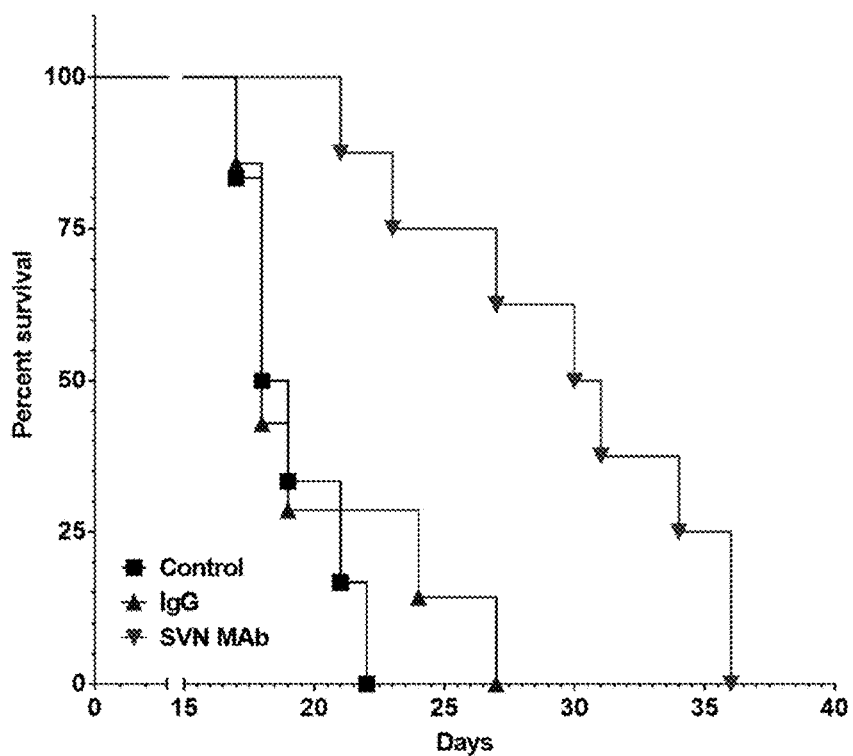
FIG. 1. Representation of effect of anti-survivin monoclonal antibody on an intracranial glioma model in C57BL/6 mice with GL261 glioma. Mice were administered anti-survivin antibody once every 7 days post tumor implantation. Percent survival is shown in as a function or time. IgG is normal mouse non-specific IgG. Control is untreated, tumor implanted mice.

The present disclosure is based on our observations that antisera from survivin peptide-vaccinated mice and purified murine monoclonal antibodies against survivin significantly inhibit tumor growth in animal models. This is surprising because survivin is an intracellular protein that is thought not to be secreted by cells or displayed on the cell surface, except within the context of MHC class I presentation. As such, antibody-mediated (passive) survivin immunotherapy would not be expected to be effective. However, we have found that it is.

This disclosure provides isolated antibodies and fragments thereof, isolated nucleic acid molecules encoding antibodies or fragments thereof, cells producing antibodies or fragments thereof, vectors or cells comprising nucleic acids encoding antibodies or fragments thereof, compositions comprising any of the foregoing, methods of making any of the foregoing, and methods of using the antibodies and fragments thereof, or nucleic acid molecules in the treatment of cancers such as those involving survivin-expressing tumors.

A description of the sequence listings with this application is as follows:

SEQ ID NO:1 is an amino acid sequence representing a 23 amino acid long fragment of human survivin.

SEQ ID NO:2 is a variant of SEQ ID NO:1 with a single amino acid change

SEQ ID NO:3 is a six amino acid long fragment of SEQ ID NO:2.

SEQ ID NO:4 is a fifteen amino acid long fragment of SEQ ID NO:2 and comprises the sequence of SEQ ID NO:3.

SEQ ID NO:5 is a ten amino acid long fragment of SEQ ID NO:2 and comprises the sequence of SEQ ID NO:3.

SEQ ID NO:6 is a nine amino acid long fragment of SEQ ID NO:2 and comprises the sequence of SEQ ID NO: 3.

SEQ ID NO:7 is an amino acid sequence for VH CDR1 for mAb 2C2E7

SEQ ID NO:8 is an amino acid sequence for VH CDR2 for mAb 2C2E7

SEQ ID NO:9 is an amino acid sequence for VH CDR3 for mAb 2C2E7

SEQ ID NO:10 is an amino acid sequence for VL CDR1 for mAb 2C2E7

SEQ ID NO:11 is an amino acid sequence for VL CDR2 for mAb 2C2E7

SEQ ID NO:12 is an amino acid sequence for VL CDR3 for mAb 2C2E7

SEQ ID NO:13 is an amino acid sequence for VH CDR1 for mAb 30H3D2

SEQ ID NO:14 is an amino acid sequence for VH CDR2 for mAb 30H3D2

SEQ ID NO:15 is an amino acid sequence for VH CDR3 for mAb 30H3D2

SEQ ID NO:16 is an amino acid sequence for VL CDR1 for mAb 30H3D2

SEQ ID NO:17 is an amino acid sequence for VL CDR2 for mAb 30H3D2

SEQ ID NO:18 is an amino acid sequence for VL CDR3 for mAb 30H3D2

SEQ ID NO:19 is an amino acid sequence for heavy chain variable region from mAb 2C2E7.

SEQ ID NO:20 is an amino acid sequence for light chain variable region from mAb 2C2E7.

SEQ ID NO:21 is an amino acid sequence for heavy chain variable region from mAb 30H3D2.

SEQ ID NO:22 is an amino acid sequence for light chain variable region from mAb 30H3D2.

SEQ ID NO:23 is a nucleotide sequence encoding the heavy chain variable region of 2C2E7 (it encodes the amino acid sequence of SEQ ID NO:19).

SEQ ID NO:24 is a nucleotide sequence encoding the light chain variable region of 2C2E7 (it encodes the amino acid sequence of SEQ ID NO:20).

SEQ ID NO:25 is a nucleotide sequence encoding the heavy chain variable region of 30H3D2 (it encodes the amino acid sequence of SEQ ID NO:21).

SEQ ID NO:26 is a nucleotide sequence encoding the light chain variable region of 30H3D2 (it encodes the amino acid sequence of SEQ ID NO:22).

SEQ ID NO:27 is a fifteen amino acid long fragment of human survivin.

While vaccines provide one way forward in anti-survivin cancer immunotherapy, there are several advantages of using a passive immunotherapy with antibodies. For example, a humanized monoclonal antibody: 1) would not be HLA-restricted (unlike peptide vaccines), 2) could potentially have immediate action against cancer cells in patients who are severely immunocompromised by their tumors, 3) would be doseable, and 4) could be used in conjunction with a vaccine or other drugs or therapies such as, for example, radiation therapy, to exploit alternative or complementary mechanisms of action. One or more the above advantages are also applicable to mAbs in general, including chimeric, human and humanized antibodies.

The term "survivin peptide" or "survivin peptides" as used herein means fragments of full length survivin and includes variants of the peptides which can generate antibodies that react with the wild type survivin, such as human survivin. The term "anti-survivin antibodies" as used herein means antibodies that are generated in response to survivin or one or more survivin peptides (including variants thereof).

In one aspect, this disclosure provides compositions comprising antibodies or fragments thereof, including human antibodies, humanized antibodies, or chimeric antibodies, which are reactive against one or more epitopes of survivin. Examples of suitable survivin epitopes or variants thereof are provided in U.S. Pat. Nos. 7,943,138, and 8,580,269, the disclosures of which are incorporated herein by reference. The compositions of the present disclosure comprise antibodies generated in response to administering a peptide that is identical to a sequence within human survivin or is a variant thereof (such as at least 95% identical). For example, antibodies may be generated in and isolated from an individual following administration of a peptide that is variant of the following portion of survivin sequence ENEPDLAQCFFCFKELEGWEPDD (SEQ ID NO:1). The variant can be ENEPDLAQMFFCFKELEGWEPDD (SEQ ID NO:2—a C to M change at position 9 of SEQ ID NO:1). The peptides administered can be from 9 to 23 (including all integers therebetween) contiguous amino acids of SEQ ID NO:2, wherein the peptide comprises the core sequence of QMFFCF (SEQ ID NO:3). Exemplary survivin peptides include DLAQMFFCFKELEGW (SEQ ID NO:4), AQMFFCFKEL (SEQ ID NO:5), and QMFFCFKEL (SEQ ID NO:6). The isolated antibodies or fragments thereof may be used without modifications, or they may be engineered, such as, for example, to generate chimeric or humanized antibodies or various fragments as described therein. In one embodiment, humanized antibodies or fragments thereof are generated that are reactive against the peptide DLAQMFFCFKELEGW (SEQ ID NO:4).

The term "Antibody" as used herein can encompass whole antibody molecules, full-length immunoglobulin molecules, such as naturally occurring full-length immunoglobulin molecules or full-length immunoglobulin molecules formed by immunoglobulin gene fragment recombinatorial processes, as well as antibody fragments. Antibody fragments can be fragments comprising at least one antibody-antigen binding site. Antibody fragments can, for example, exhibit specific binding to survivin or fragments thereof comprising the motif DLAQCFFCFKELEGW (SEQ ID NO:27). The term "antibody" can include e.g. monoclonal, polyclonal, multispecific (for example bispecific), recombinant, human, chimeric and humanized antibodies. The term "antibody" can also encompass recombinantly expressed antigen binding proteins and antigen binding synthetic peptides. Further, the term "antibody" can encompass minibodies, and diabodies, all of which preferably exhibit specific binding to survivin of a fragment thereof, especially human survivin. The term "antibody", as used herein, can also encompass immunoglobulins produced in vivo, as well as those produced in vitro, such as, for example, by a hybridoma. An antibody of the present disclosure may be modified by, for example, acetylation, formylation, amidation, phosphorylation, or polyethylene glycolation (PEGylation), as well as glycosylation. The term "an antibody" as used herein is intended to cover all antibodies disclosed herein. For example, the term "an antibody" can refer to monoclonal, polyclonal, chimeric, human, or humanized antibodies, or antigen (i.e., survivin) binding fragments thereof.

Administration of survivin peptides can be used for generation of polyclonal antibodies. For example, suitable animals can be administered one or more survivin peptides and serum can be collected. Further, human anti-survivin antibody-expressing cells can be isolated from immunized animals or patients vaccinated with survivin or survivin peptides—for example, from individuals who may be participating in clinical trials. IgG+ memory B cells from patient samples can be expanded and induced to differentiate into IgG-secreting cells, which can be screened for high-affinity target (survivin peptide) binding. The cells can also be used for generation of hybridomas. Variable regions of antibody genes can be cloned from isolated cells by RT-PCR using the PIPE method (Dodev T S et al. (2014) Scientific Reports 4, 5885. doi:10.1038/srep058853). Recombinant human, humanized or chimeric mAbs can be constructed from these molecules and can be expressed and screened in functional and binding affinity assays and for anti-tumor activity. In this regard, we have been able to detect specific antibodies by ELISA in several patients in a clinical study. Samples can be frozen for later use for isolation of memory B cells.

The antibodies of the disclosure may be whole immunoglobulin molecules such as polyclonal or monoclonal antibodies or may be antigen-binding fragments thereof, including but not limited to, Fab, F(ab'), F(ab')2, Fv, dAb, Fd, CDR fragments, single-chain antibodies (scFv), bivalent single-chain antibodies, single-chain phage antibodies, diabodies, nanobodies and the like. The fragments of the antibodies may be produced synthetically or by enzymatic or chemical cleavage of intact immunoglobulins or may be genetically engineered by recombinant DNA techniques. These techniques are well known in the art.

In one embodiment, this disclosure provides isolated antibodies. By the term "isolated" it is meant that the antibody or the fragment thereof, is separated and/or recovered from its natural environment. The isolation of the antibody from its natural environment can be such that the antibody can be used without interference from other active agents (such as other proteins) that normally are present in its natural environment.

In one embodiment, this disclosure provides generating and isolating single domain antibodies or nanobodies produced by camelids in response to introducing survivin or survivin peptides into the camelids. The nanobodies are typically heavy chain antibodies and thus contain heavy chain homodimers and do not contain antibody light chains. These antibodies typically comprise a single variable domain and two constant domains (CH2 and CH3).

The antibodies of the present disclosure may be obtained from a human or a non-human animal. In many mammals, intact immunoglobulins have two heavy chains and two light chains. Each of the light chains is covalently linked to a heavy chain by a disulfide bond. The two heavy chains are linked to each other by additional disulfide bonds. The light chain typically has one variable domain (VL) and one constant domain (CL). The heavy chain can also have one variable domain (VH). The variable domains contain complementarity-determining regions (CDRs). The heavy chain can further have three or four constant domains (CHI, CH2, CH3 and CH4). The variability of the constant domains results is various isotypes such as IgA, IgD, IgE, IgG, and IgM.

The CDRs are primarily responsible for binding to an epitope of an antigen. The CDRs of each chain are typically referred to as CDR1, CDR2, and CDR3, numbered sequentially starting from the N-terminus, and are typically identified by the chain in which the particular CDR is located. Thus, a $V_H$ CDR3 (or VH-CDR3) is located in the variable domain of the heavy chain of the antibody in which it is found, whereas a $V_L$ CDR1 (or VL-CDR1) is the CDR1 from the variable domain of the light chain of the antibody in which it is found. An antibody that binds survivin or survivin peptides, for example, will have a specific $V_H$ region and the $V_L$ region sequence, and thus specific CDR sequences. Antibodies with different specificities (i.e. different combining sites for different antigens) have different CDRs.

The terms $V_H$ or VH as used herein refer to the variable region of an immunoglobulin heavy chain, including a heavy chain of an Fv, scFv, dsFv or Fab, and the terms $V_L$ or VL refer to the variable region of an immunoglobulin light chain, including a light chain of an Fv, scFv, dsFv or Fab.

The term "monoclonal antibody" refers to an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. For example, mice (or other suitable animals) may be immunized with one or more survivin peptides and then ascites fluid samples can be collected. The samples can be screened and selected to develop a panel of monoclonal antibodies and corresponding hybridoma cell lines. Murine (or other) monoclonal antibodies may be isolated or generated and then humanized, if desired.

An antibody of the present disclosure can be an antibody of any class. For example, an antibody of the present invention can be an antibody isotype IgG1, IgG2, IgG3, IgG4, IgM, IgA, IgD or IgE. For example, the antibody can be IgG2b. The term "isotype", as used herein, can in particular refer to the antibody class (such as e.g. IgG) that is encoded by heavy chain constant region genes. Sequences of human immunoglobulin constant regions are known in the art and are available in public databases such as National Center for Biotechnology Information (NCBI), U.S. National Library of Medicine.

The term "chimeric antibody" refers to an antibody which has framework residues from one species, such as human, and CDRs (which generally confer antigen binding) from another species, such as a murine antibody that specifically binds survivin. In a chimeric antibody, some portions of the heavy and/or light chains may be identical or homologous to sequences from a particular species while other portions may be identical or homologous to sequences from a different species. Chimeric antibodies generally exhibit decreased immunogenicity and increased stability. Techniques for cloning murine immunoglobulin variable domains known in the art—such as, for example, see Orlandi et al., Proc. Natl Acad. Sci. USA 86: 3833 (1989), and Leung et al., Hybridoma 13:469 (1994). As an example of a chimeric antibody, polynucleotides encoding the variable domains of the light chain or the heavy chain of an antibody derived from an animal (e.g., mouse, rat, or chicken) other than human can be linked to polynucleotides encoding the constant domains of the light chain or the heavy chain derived from a human antibody to produce a polynucleotide (such as DNA) encoding a chimeric antibody. Examples of chimeric antibodies include those comprising SEQ ID NOs:19 and 20, and those comprising SEQ ID NOs:20 and 21.

A "human" antibody (also called a "fully human" antibody) is an antibody that includes human framework regions and all of the CDRs from a single or different human immunoglobulins. Thus, frameworks from one human antibody can be engineered to include CDRs from a different human antibody. Methods for producing human antibodies are known in the art—such as, for example, see Mancini et al., 2004, New Microbiol. 27:315-28; Conrad and Scheller, 2005, Comb. Chem. High Throughput Screen. 8:117-26.

A "humanized antibody" is typically a human antibody that has one or more amino acid residues imported into it (i.e., introduced into it) from a source that is non-human. For example, a humanized antibody is a recombinant protein in which the CDRs of an antibody from a species such as rodent, rabbit, dog, goat, or horse are imported into human heavy and light variable domains. The constant domains (also referred to as framework regions) of the antibody molecule are generally the same as those of a human antibody. The non-human immunoglobulin providing the CDRs can be termed as "donor" and the human immunoglobulin providing the framework can be termed as "acceptor". For example, all the CDRs can be from the donor immunoglobulin in a humanized immunoglobulin. Constant regions need not be always present, but if they are, they can be substantially identical to human immunoglobulin constant regions, i.e., at least about 85-90%, such as about 95% or more identical. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089, and U.S. Publication No. 2010/0196266). For example, murine monoclonal antibodies may be isolated or generated and then humanized. Examples of humanized antibodies include those comprising CDRs having sequences of SEQ ID NOs:7 through 12, and those comprising CDRs having sequences of SEQ ID NOs:13 through 18.

Antibody fragments can be produced by enzymatic digestion. For example, papain digestion of antibodies produces two identical antigen-binding fragments, called "Fab" fragments, and a "Fc" fragment. The Fab fragment contains an entire L chain and the variable region domain of the H chain (VH), and the first constant domain of one heavy chain. Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is capable of cross-linking antigen. "Fv" is the minimum antibody fragment that contains a complete antigen-recognition and -binding site and single-chain Fv also abbreviated as "sFv" or "scFv" are antibody fragments that comprise the VH and VL antibody domains connected into a single polypeptide chain. The term "diabodies" refers to small antibody fragments prepared by constructing sFv fragments with short linkers between the VH and VL domains such that interchain but not intra-chain pairing of the V domains is achieved, resulting in a bivalent fragment, i.e., fragment having two antigen-binding sites. A single domain antibody (sdAb) is an antibody fragment which has a single monomeric variable antibody domain. ScAbs can be made from heavy-chain antibodies found in camelids. An antibody fragment can be a single variable region or a peptide consisting of or comprising a single CDR. A single-chain antibody has a heavy chain variable domain and a light chain variable domain linearly linked to each other via a linker. A polynucleotide (such as DNA) encoding the single-chain antibody can be produced by binding a polynucleotide encoding the heavy chain variable domain, a polynucleotide encoding the linker (typically 10-20 nucleotides), and a polynucleotide encoding the light chain variable domain, with the heavy chain variable domain and the light chain variable domain being both derived from a human antibody.

The antibodies of the present invention can be bispecific or multispecific. Bispecific antibodies (diabodies) are antibodies that have binding specificities for at least two different epitopes of an antigen, such as two different epitopes of survivin. For example, a polynucleotide (such as DNA) encoding a bispecific antibody can be produced by, for example, linking in order a polynucleotide encoding a heavy chain variable region A, a polynucleotide encoding a light chain variable region B, a polynucleotide encoding a heavy chain variable domain B, and a polynucleotide encoding a light chain variable domain A. Preferably, the heavy chain variable domain and the light chain variable domain are both derived from a human antibody.

The present disclosure provides variants of sequences set forth in SEQ ID NOs: 1 through 29. For example, variants can have at least 90%, at least 95%, at least 98% or at least 99% sequence identity to the sequences disclosed in SEQ ID NOs:1-27.

The present disclosure provides T cells transduced to express a chimeric antigen receptor (CAR). CAR molecules of the present disclosure combine antibody-based specificity for survivin with a T cell receptor-activating intracellular domain to generate a chimeric protein that exhibits specific anti-survivin, and therefore, anti-tumor cellular immune activity. A CAR molecule can comprise one or more CDRs of the heavy or light variable regions. This disclosure further provides T cells genetically modified to stably express the CAR. T cells expressing a CAR are referred to herein as CAR T cells or CAR modified T cells. For example, T cells can be genetically modified to stably express the CAR that combines a survivin recognition domain of a specific antibody, such as a monoclonal antibody described herein, with an intracellular domain of the CD3-zeta chain into a single chimeric protein.

As an example, this disclosure provides monoclonal antibodies, which can be isolated monoclonal antibodies, which specifically bind to survivin, which can be human survivin. As an example, a mAb designated 2C2 and a mAb designated H30 (or 30H3) are provided. A subclone of mAb 2C2 used for final antibody sequencing and IgG purification was designated 2C2E7, and a subclone of mAb H30 used for final antibody sequencing and IgG purification was designated 30H3D2. An antibody comprises a heavy chain variable region and a light chain variable region. The heavy chain variable region comprises a VH CDR1, a VH CDR 2, and a VH CDR3, and the light chain variable region comprises a VL CDR1, a VL CDR2, and a VL CDR3. As an example, the VH CDR1 has an amino acid sequence TYGMS (SEQ ID NO:7), the VH CDR2 has an amino acid sequence WINPYSGVPTYAVDFKG (SEQ ID NO:8), and the VH CDR3 has an amino acid sequence GGRRGDFGY (SEQ ID NO:9); and the VL CDR1 has an amino acid sequence SASSSISYMH (SEQ ID NO:10), the VL CDR2 has an amino acid sequence DTSKLAS (SEQ ID NO:11), and the VL CDR3 has an amino acid sequence HQRSSHHT (SEQ ID NO:12). As another example, the VH CDR1 has an amino acid sequence SYGMS (SEQ ID NO:13), the VH CDR2 has an amino acid sequence TISSGGSHTYYPDSVRG (SEQ ID NO:14), and the VH CDR3 has an amino acid sequence HPIYYYISSYAMDY (SEQ ID NO:15); and the VL CDR1 has an amino acid sequence RSSQSLVHSTGNTYLH (SEQ ID NO:16), the VL CDR2 has an amino acid sequence KVSNRFS (SEQ ID NO:17), and the VL CDR3 has an amino acid sequence SQSTHVPPT (SEQ ID NO:18).

An antibody of the present disclosure can be an antibody which has VH CDRs that have 1 or 2 amino acids that are different than the sequence set forth in SEQ ID NOs:7, 8, 9, and/or which has VL CDRs that have 1 or 2 amino acids that are different than the sequence set forth in SEQ ID NOs:10, 11, 12. An antibody of the present disclosure can be an antibody which has VH CDRs that have 1 or 2 amino acids that are different than the sequence set forth in SEQ ID NOs:13, 14, 15, and/or which has VL CDRs that have 1 or 2 amino acids that are different than the sequence set forth in SEQ ID NOs:16, 17, 18.

An antibody of the present disclosure can be an antibody wherein the heavy chain variable region comprises the sequence of SEQ ID NO: 19, and the light chain variable region comprises the sequence of SEQ ID NO: 20. In the sequence of SEQ ID NO:19, amino acids 1 through 19 represent a leader sequence, amino acids 20 through 49 represent framework region (FR) 1, amino acids 50 through 54 represent CDR1, amino acids 55 through 68 represent FR2, amino acids 69 through 85 represent CDR2, amino acids 86 through 117 represent FR3, amino acids 118 through 126 represent CDR3, and amino acids 127 through 137 represent FR4. In the sequence of SEQ ID NO: 20, amino acids 1 through 22 represent a leader sequence, amino acids 23 through 45 represent FR1, amino acids 46 through 55 represent CDR1, amino acids 56 through 70 represent FR2, amino acids 71 through 77 represent CDR2, amino acids 78 through 109 represent FR3, amino acids 110 through 117 represent CDR3, and amino acids 118 through 127 represent FR4.

An antibody of the present disclosure can be an antibody comprising a heavy chain variable region comprising the sequence of SEQ ID NO:21, and a light chain variable region comprising the sequence of SEQ ID NO:22. In the sequence of SEQ ID NO:21, amino acids 1 through 19 represent a leader sequence, amino acids 20 through 49 represent FR1, amino acids 50 through 54 represent CDR1, amino acids 55 through 68 represent FR2, amino acids 69 through 85 represent CDR2, amino acids 86 through 117 represent FR3, amino acids 118 through 131 represent CDR3, and amino acids 132 through 142 represent FR4. In the sequence of SEQ ID NO: 22, amino acids 1 through 19 represent a leader sequence, amino acids 20 through 42 represent FR1, amino acids 43 through 58 represent CDR1, amino acids 59 through 73 represent FR2, amino acids 74 through 80 represent CDR2, amino acids 81 through 112 represent FR3, amino acids 113 through 121 represent CDR3, and amino acids 122 through 131 represent FR4.

An antibody of the present disclosure can be an antibody comprising a heavy chain variable region comprising a sequence of SEQ ID NO:19 and a light chain variable region comprising a sequence of SEQ ID NO:20, or variants thereof that have 90% to 99% sequence identity. An antibody of the present disclosure can be an antibody comprising a heavy chain variable region comprising a sequence of SEQ ID NO:21 and a light chain variable region comprising a sequence of SEQ ID NO:22, or variants thereof that have 90% to 99% sequence identity. An antibody can be an antibody comprising a heavy chain variable region comprising a sequence of SEQ ID NO:19 excluding the leader sequence (i.e., excluding amino acids 1 through 19) and/or a light chain variable region comprising a sequence of SEQ ID NO:20 excluding the leader sequence (i.e., excluding amino acids 1 through 22), or variants thereof that have 90% to 99% sequence identity. An antibody of the present disclosure can be an antibody comprising a heavy chain variable region comprising a sequence of SEQ ID NO:21 excluding the leader sequence (i.e., excluding amino acids 1 through 19) and/or a light chain variable region comprising a sequence of SEQ ID NO:22 excluding the leader sequence (i.e., excluding amino acids 1 through 19), or variants thereof that have 90% to 99% sequence identity.

An antibody of the present disclosure can be an antibody comprising a heavy chain variable region which has a sequence which is at least 90%, 91%, 92%, 93%, 94%, 95%, 96%, 97%, 98% or 99% identical to SEQ ID NO:19 and which comprises a CDR1 having a sequence of SEQ ID NO:7, a CDR2 having a sequence of SEQ ID NO:8, and a CDR3 having a sequence of SEQ ID NO:9, and/or a light chain variable region which as a sequence which is at least 90%, 91%, 92%, 93%, 94%, 95%, 96%, 97%, 98% or 99% identical to SEQ ID NO:20 and which comprises a CDR1 having a sequence of SEQ ID NO:10, a CDR2 having a sequence of SEQ ID NO:11, and a CDR3 having a sequence of SEQ ID NO:12.

An antibody of the present disclosure can be an antibody comprising a heavy chain variable region which has a sequence which is at least 90%, 91%, 92%, 93%, 94%, 95%, 96%, 97%, 98% or 99% identical to SEQ ID NO:21 and which comprises a CDR1 having a sequence of SEQ ID NO:13, a CDR2 having a sequence of SEQ ID NO:14, and a CDR3 having a sequence of SEQ ID NO:15, and/or a light chain variable region which as a sequence which is at least 90%, 91%, 92%, 93%, 94%, 95%, 96%, 97%, 98% or 99% identical to SEQ ID NO:20 and which comprises a CDR1 having a sequence of SEQ ID NO:16, a CDR2 having a sequence of SEQ ID NO:17, and a CDR3 having a sequence of SEQ ID NO:18.

An antibody of the present disclosure can be a chimeric, human or humanized antibody comprising a heavy chain variable region comprising CDR1, CDR2 and CDR3 having the sequences of SEQ ID NOs: 7, 8 and 9 respectively, and a light chain variable region comprising CDR1, CDR2, and CDR3 having the sequences of SEQ ID NOs: 10, 11 and 12 respectively, or comprising a heavy chain variable region comprising CDR1, CDR2 and CDR3 having the sequences of SEQ ID NOs: 13, 14 and 15 respectively, and a light chain variable region comprising CDR1, CDR2, and CDR3 having the sequences of SEQ ID NOs: 16, 17 and 18 respectively.

The present disclosure also provides isolated nucleotide sequences encoding all or portions of heavy chain variable regions for survivin specific antibodies. For example, the present disclosure provides an isolated nucleic acid molecule comprising the sequence of SEQ ID NOs: 23 or 25. An isolated nucleotide molecule of the present disclosure can encode all or portions of light chain variable regions for survivin specific antibodies. For example, the isolated nucleic acid molecule can comprise the sequence of SEQ ID NOs: 24 or 26. Variants of nucleic acid molecules can have at least 90% to at least 99% identity with the sequences of SEQ ID NOs: 23 or 25 for the heavy chain variable region or SEQ ID NOs: 24 or 26 for the light chain variable region.

The present disclosure also provides isolated nucleic acid molecules comprising or consisting of the sequence encoding one or more CDRs that recognize a survivin epitope— such as for example, sequences encoding SEQ ID NOs: 7 to 18. A nucleic acid molecule can consist of any of the sequences of SEQ ID NOs: 7 to 18, or a nucleic acid molecule can comprise one or more sequences of SEQ ID NOs: 7 to 18 and further comprise additional 1 to 50 nucleotides—generally flanking the sequences.

The disclosure provides cells comprising an expression vector or other polynucleotide sequence encoding the antibodies provided herein (including mAbs) or survivin binding fragments thereof. Nucleotide sequences encoding the mAbs or survivin binding fragments thereof can be expressed using any suitable expression vector, many of which are known in the art and/or are commercially available. A vector generally includes nucleic acid sequences, such as origin or replication that enables it to replicate in a host cell. A vector can also include selectable marker genes. Heavy and light chains can be expressed on a single expression vector, such as a plasmid or the heavy and light chains can be expressed on distinct plasmids in the same cell, after which the expressed heavy and light chains can form the conventional mAb architecture. The mAbs or survivin binding fragments thereof can be isolated and/or purified using conventional techniques, given the benefit of the present disclosure.

The isolated monoclonal antibodies or fragments thereof can be labeled, such as with enzymatic, fluorescent or radioactive tags or can be conjugated to effector molecules such as, for example, toxins.

The present disclosure provides pharmaceutical compositions comprising the antibodies or fragments thereof, and pharmaceutically suitable carrier. Suitable carriers include excipients, or stabilizers which are nontoxic to recipients at the dosages and concentrations employed, and include buffers such as acetate, Tris, phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; and/or non-ionic surfactants such as Tween or polyethylene glycol (PEG). The pharmaceutical compositions may comprise other therapeutic agents.

Compositions of the present disclosure can comprise one type of monoclonal antibody or more than one type of monoclonal antibody. A composition of the disclosure can have one or more of an antibody or fragment or variant thereof. A composition can have a monoclonal and a polyclonal antibody. A composition can comprise one or more subtypes of antibodies. For example, a composition can comprise a mixture of IgG or IgM or a mixture of one or more of IgG1, IgG2, and IgG2b. A composition of the present disclosure can comprise an antibody as the only active ingredient, wherein the antibody may be monoclonal, polyclonal, chimeric, human, humanized or combinations thereof. By "active ingredient" is meant that the ingredient has an anti-tumor effect by inhibiting tumor growth.

A pharmaceutical composition of the disclosure can comprise one or more antibodies at a concentration range from 0.1 mg/ml to 100 mg/ml, 1 mg/ml to 10 mg/ml, 1 mg/ml to 50 mg/ml, 1 mg/ml to 100 mg/ml, 10 mg/ml to 100 mg/ml, or 50 mg/ml to 100 mg/ml of each of the antibodies or total antibodies. For example, a pharmaceutical composition of the disclosure can comprise at least or about 0.1 mg/ml, at least or about 1 mg/ml, at least or about 5 mg/ml, at least or about 10 mg/ml, at least or about 50 mg/ml, at least or about 100 mg/ml of an antibody.

The compositions of the present disclosure may be administered by routine methods known in the art. For example, the compositions comprising antibodies or fragments thereof may be administered via intravenous, intramuscular, intraperitoneal, intracerebrospinal, subcutaneous, intra-articular, intrasynovial, intrathecal, oral, topical, or inhalation routes, or by intracerebral or intra-spinal convection enhanced delivery or direct intratumoral injection. The antibodies may be administered parenterally directly at the target site (such as at or within a tumor). The compositions may be introduced as a single administration or as multiple administrations and may be introduced in a continuous manner over a period of time. In one embodiment, the composition may be administered daily for a period of at least 2 days such as, for example, for a period of 2-30 days (and all periods therebetween). In one embodiment, it is administered daily for 7-10 days. It may alternatively be administered at desired intervals (such as every 2, 3, 4, 5 days and the like).

It will be recognized by those of skill in the art that the form and character of the particular dosing regimen employed in the method of the invention will be dictated by the route of administration and other well-known variables, such as the size of the individual and the stage of the disease. Further, the compositions can be provided in the form of unit dosage forms for administration to an individual in need of treatment. Antibodies can be provided in a lyophilized form to be reconstituted prior to administration. The reconstitution medium can be sterile 0.9% saline solution or a suitable physiological buffer or water, or any other solution known in the art for reconstituting proteins prior to administration.

The disclosure also provides kits which can be used for administration to individuals in need of treatment. A kit, for example, can comprise one or more antibodies, which may be in a lyophilized form, optionally reconstitution media, and instructions for administration. A kit can comprise a single dose or multiple doses.

The disclosure provides a method for treating tumors, such as tumors that comprise survivin-expressing cells. Such tumors may be referred to herein as "survivin-expressing tumors". The term "treatment" refers to reduction in one or more symptoms or features associated with the presence of the particular condition being treated. Treatment does not necessarily mean complete remission, nor does it preclude recurrence or relapses. For example, the present disclosure provides a method for reducing the size of a tumor or arresting the growth of a tumor or reducing the rate of growth of a tumor (such as a tumor comprising survivin-expressing cells) or reducing any other symptom that is associated with an individual being afflicted with the tumor—all of which are considered as "treatment"—comprising administering to an individual in need of treatment, a therapeutically effective amount of a composition comprising antibodies, or fragments thereof as described herein. In one embodiment, the method is a method of passive immunization.

Examples of tumors that can be treated by the present compositions include, but are not limited to, glioma, glioblastoma, medulloblastoma, multiple myeloma, melanoma, meningioma, breast adenocarcinoma, ovarian carcinoma, prostate carcinoma, leukemia, lymphoma, colon carcinoma, pancreatic cancer, hepatic cancer, kidney cancer, sarcoma and the like.

The method of the invention can be performed in conjunction with use of survivin peptides as a vaccine. The compositions of the invention can be administered prior to, concurrently, or subsequent to other therapies.

In one aspect, the present disclosure provides compositions comprising an isolated antibody which is reactive against one or more epitopes of survivin wherein the isolated antibody or the antigen-binding fragment thereof binds to one or more epitopes of survivin. The antibody may be generated in response to administration of a peptide having the sequence ENEPDLAQMFFCFKELEGWEPDD (SEQ ID NO:2), or a fragment thereof (such as SEQ ID NO:4), wherein the fragment has from 9 to 23 (including all integers therebetween) contiguous amino acids of SEQ ID NO:2, and wherein the peptide comprises the core sequence of QMFFCF (SEQ ID NO:3). The composition may be such that the only antibody or antibodies present is/are the isolated antibody/antibodies generated in response to administration of survivin peptides. The composition may have other protein such as carrier proteins. The antibody may be a chimeric, human or a humanized antibody. The antibody may be a monoclonal or a polyclonal antibody, or a single chain, or multispecific antibody.

Reactivity of antibodies toward specific antigens can be measured by routine methods such as, for example, ELISA. Reactivity is an indication of the binding affinity. Binding affinity can also be measured by antigen/antibody dissociation rates or competition radioimmunoassays and the like. Specific binding of an antibody to an antigen means it binds the antigen with high affinity and does not specifically bind to unrelated antigens.

In one aspect, the disclosure provides a method of passive immunization comprising administering to an individual in need of treatment, a therapeutically effective amount of the composition comprising one or more antibodies generated in response to administration of a peptide having the sequence ENEPDLAQMFFCFKELEGWEPDD (SEQ ID NO:2), or a fragment thereof (such as SEQ ID NO:4), wherein the fragment has from 9 to 23 (including all integers therebetween) contiguous amino acids of SEQ ID NO:2, and wherein the peptide comprises the core sequence of QMFFCF (SEQ ID NO:3), and which antibodies have been isolated from the subject (human or non-human) they were raised in or obtained from a hybridoma supernatant, or may be engineered antibodies using sequences from the isolated antibodies.

The following examples are meant to illustrate, and are not intended to be limiting.

Example 1

This example describes animal studies demonstrating an effect of anti-survivin antibodies on tumor growth.

Mice are administered DLAQMFFCFKELEGW-keyhole limpet hemocyanin (KLH) (SurVaxM) (SVN53-67/M57-KLH) (SEQ ID NO:4) as an immunization. Mice were injected subcutaneously with 100 µg of peptide. Mice were repeat immunized once every 7 days for a 28 day period. Two weeks after final immunization mice were euthanized via $CO_2$ asphyxiation and blood was collected through cardiac puncture. Blood was allowed to clot and is centrifuged at 10,000×g to produce clarified serum. Survivin anti-serum was used to passively immunize mice in tumor implantation models.

Intracranial subcutaneous tumor models were used to show efficacy of anti-survivin antibody against tumor growth. Intracranial studies used anesthetized C57BL/6 mice implanted with $1×10^5$ GL261 glioma cells through a 26 gauge needle advanced through an intracranial burr hole placed at 1 mm anterior, 2 mm lateral and 3 mm in depth to the bregma skull suture as anatomical reference point. After 3 days mice were randomized into groups and injected with 10 µg of anti-survivin antibody or 10 µg of normal IgG for control. Antibodies were administered every 5 days for a total of 4 doses in a 20 day period. Mice were followed for signs of neurological deficits as an indicator of tumor growth and sacrificed according to established criteria. Data is represented as survival and shown in Kaplan-Meier plot, $p<0.0001$.

Subcutaneous tumor models were established through implantation of $1×10^6$ GL261 glioma cells subcutaneously right flank through a 23 gauge intradermal needle. Tumors were allowed to grow for 7 days until they reached approximately 2 mm in diameter. Mice were then on day 7 administered 100 µg SurVaxM (SVN53-67/M57-KLH) survivin vaccine; or 50 µl anti-survivin antibody in the form of mouse sera from mice that had been previously administered SurVaxM or 10 µg mAb (antibody) derived from non-tumor bearing pooled mice receiving the SurVaxM survivin vaccine, or a monoclonal antibody reactive against survivin. Treatment was re-administered every 7 days for 4 doses over a 28 day period. Tumors were measured daily and volumes calculated using the formula "V=XY2/2". Mice were followed for 60 days. Data is shown as combined tumor volumes (FIG. 1) and individual tumor progression (FIG. 2), $p<0.0001$. The SurVaxM vaccine refers to a vaccine in which the peptide has the sequence DLAQMFFCFKELEGW (SEQ ID NO: 4).

Figure 2:
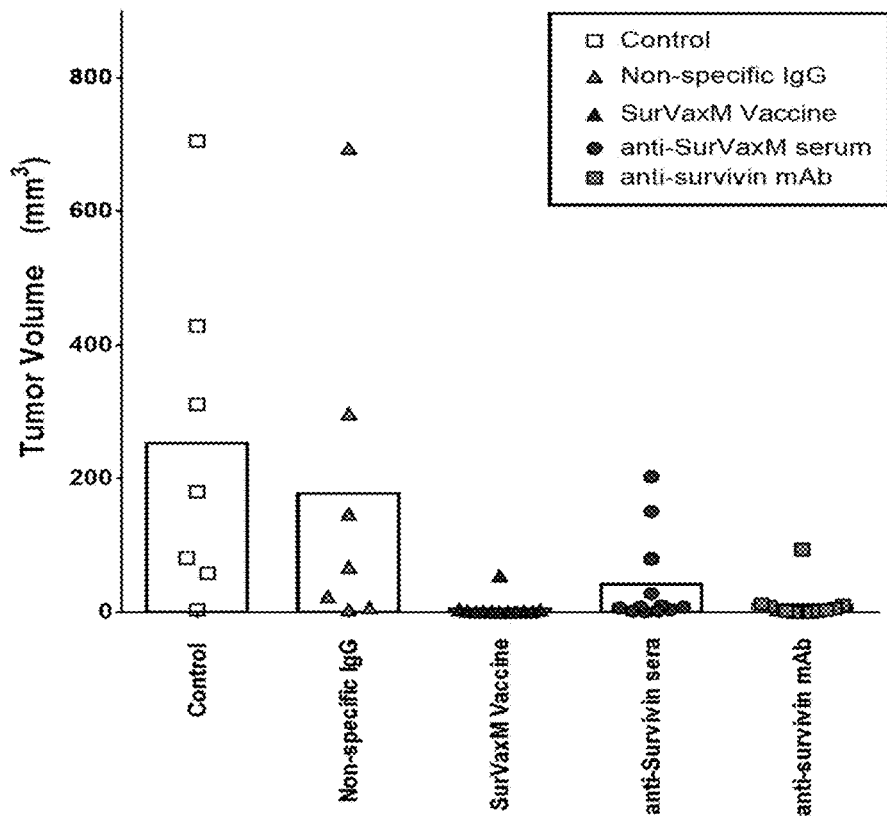
FIG. 2. Representation of effect of anti-survivin polyclonal and monoclonal antibodies on a subcutaneous tumor model in C57BL/6 mice with GL261 glioma. Mice were administered the indicated treatments once every 7 days post tumor implantation. SurVaxM is the survivin vaccine; anti-survivin sera (antibody) was derived from non-tumor bearing pooled mice receiving active survivin vaccine or survivin peptides. Control is untreated, tumor implanted mice.
Figure 3:
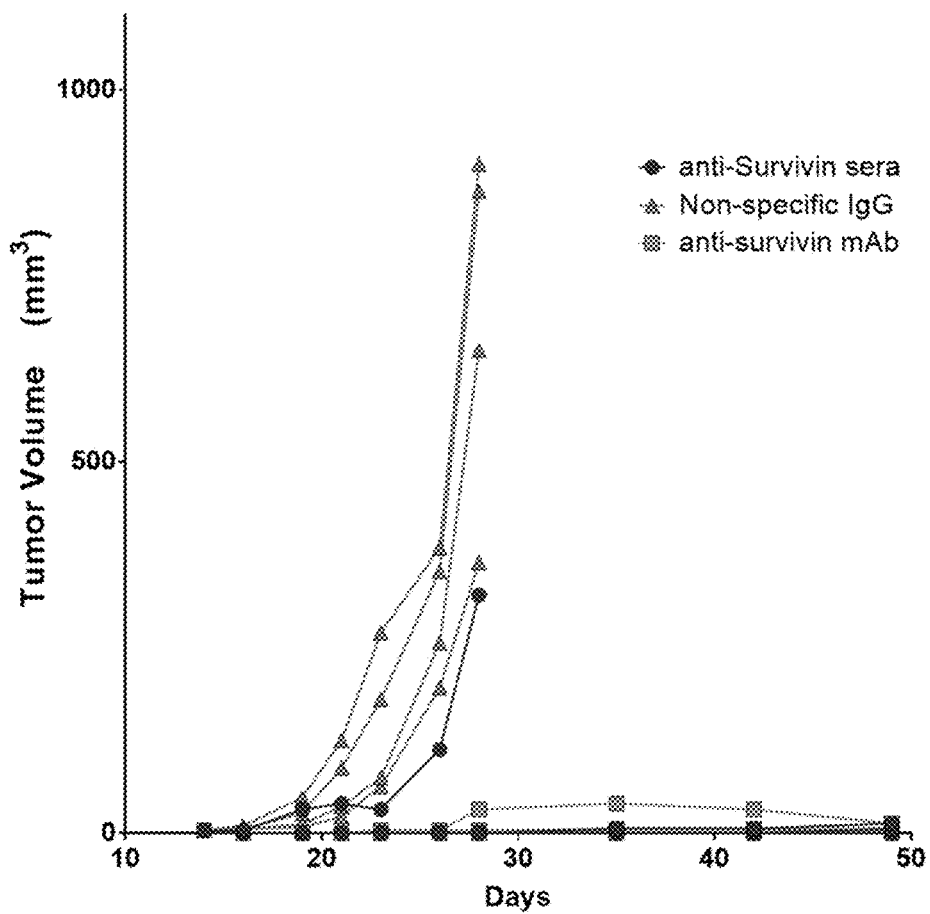
FIG. 3. Representation of effect of anti-survivin polyclonal antibodies on a subcutaneous tumor model in C57BL/6 mice with GL261 glioma. Mice were administered the indicated treatments once every 7 days post tumor implantation. SurVaxM is the survivin vaccine; anti-survivin sera (antibody) was derived from non-tumor bearing pooled mice receiving active SurVaxM vaccine. Mice were followed up to 50 days.
Figure 4:
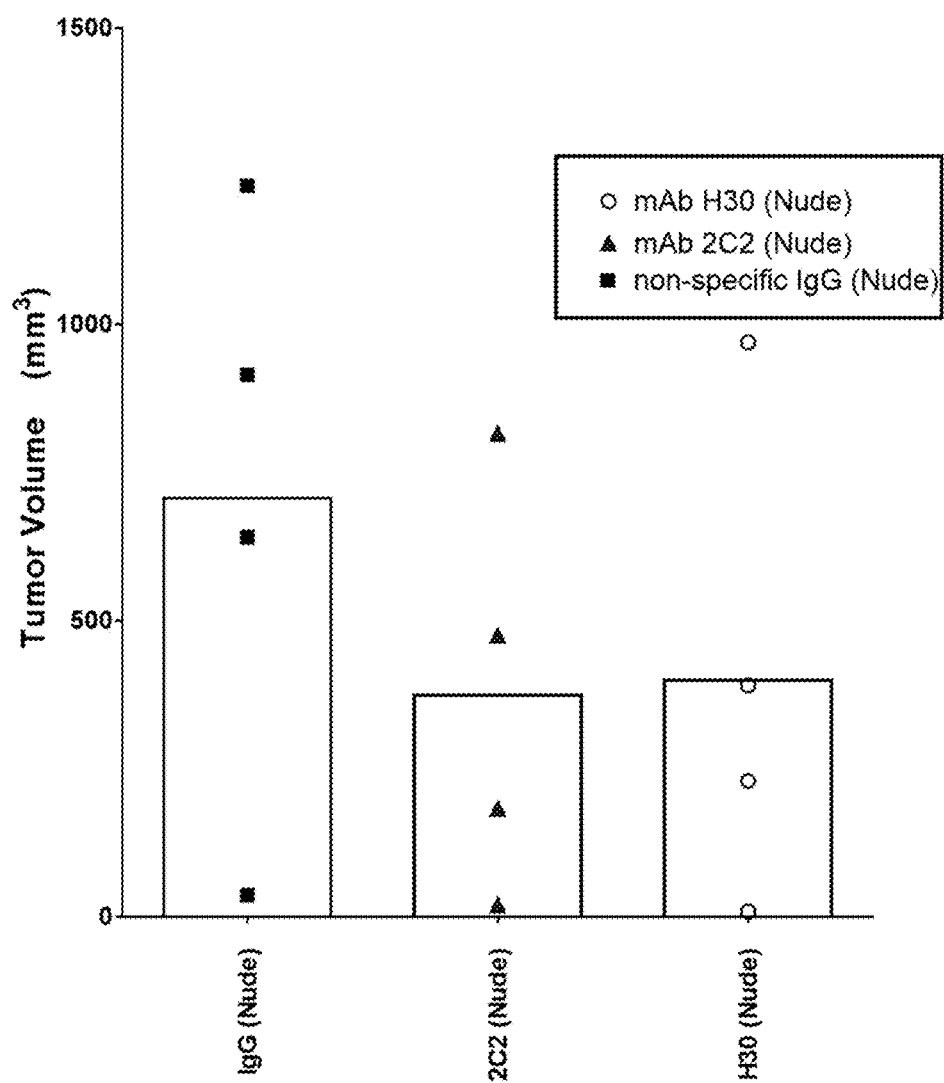
FIG. 4. Representation of effect of two monoclonal antibodies against B16 murine melanoma in Nude (immunocompromised) mice. Tumor volume is shown for groups receiving non-specific IgG, mAb 2C2 and mAb H30. Each point represents one animal.
Figure 5:
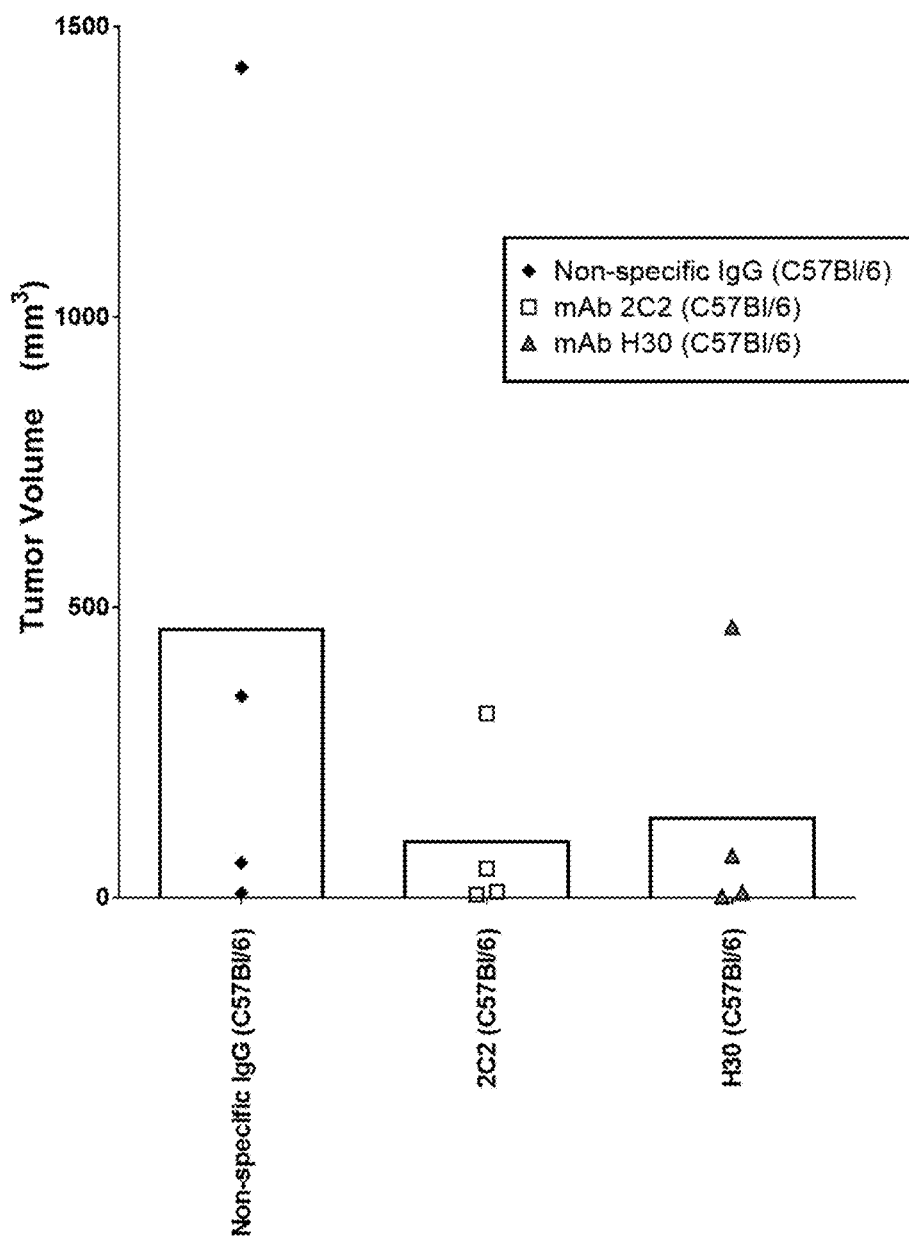
FIG. 5. Representation of effect of two monoclonal antibodies against B16 murine melanoma in C57B1/6 (immunocompetent) mice. Tumor volume is shown for groups receiving non-specific IgG, mAb 2C2 and mAb H30. Each point represents one animal.
Figure 6:
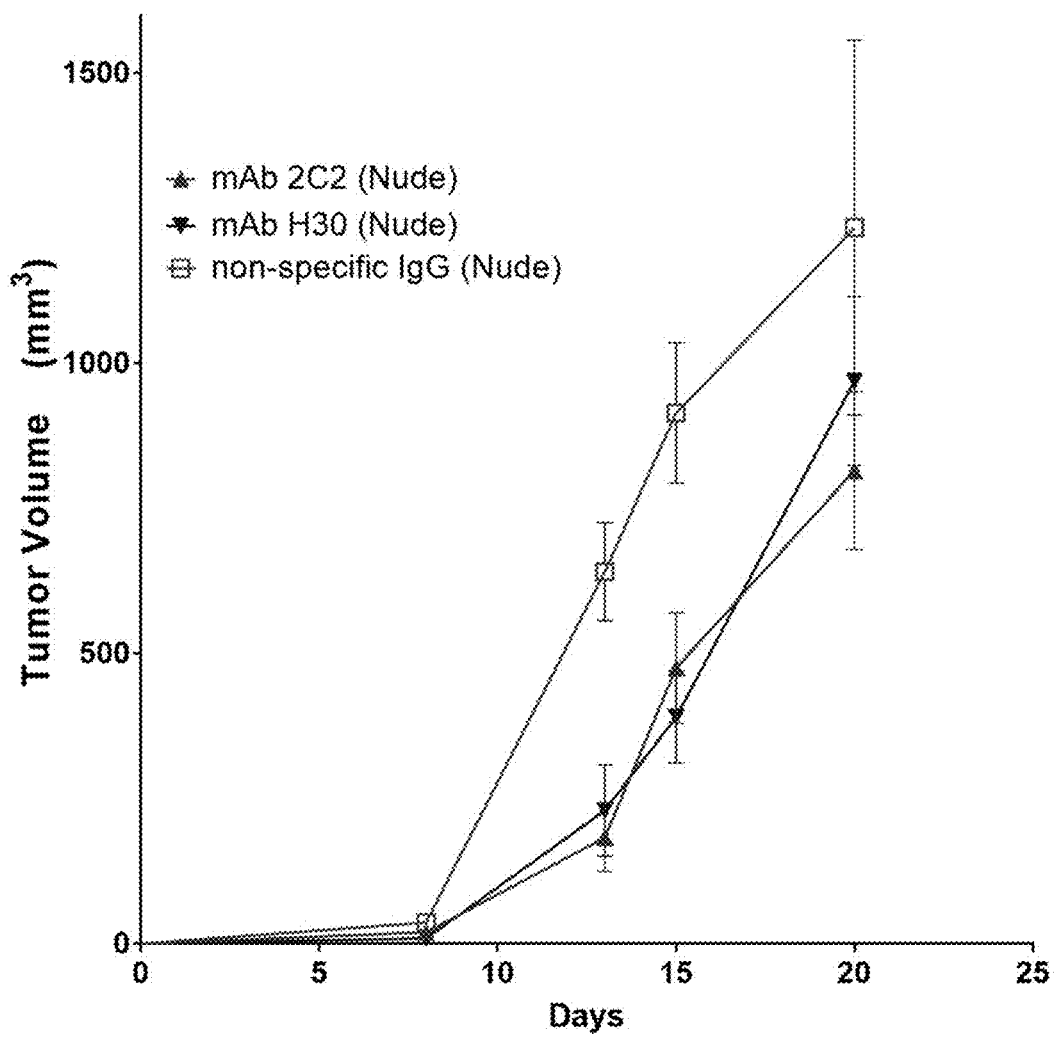
FIG. 6. Representation of effect of two monoclonal antibodies against B16 murine melanoma in Nude (immunocompromised) mice as a function of time. Tumor volume is shown for groups receiving non-specific IgG, mAb 2C2 and mAb H30.
Figure 7:
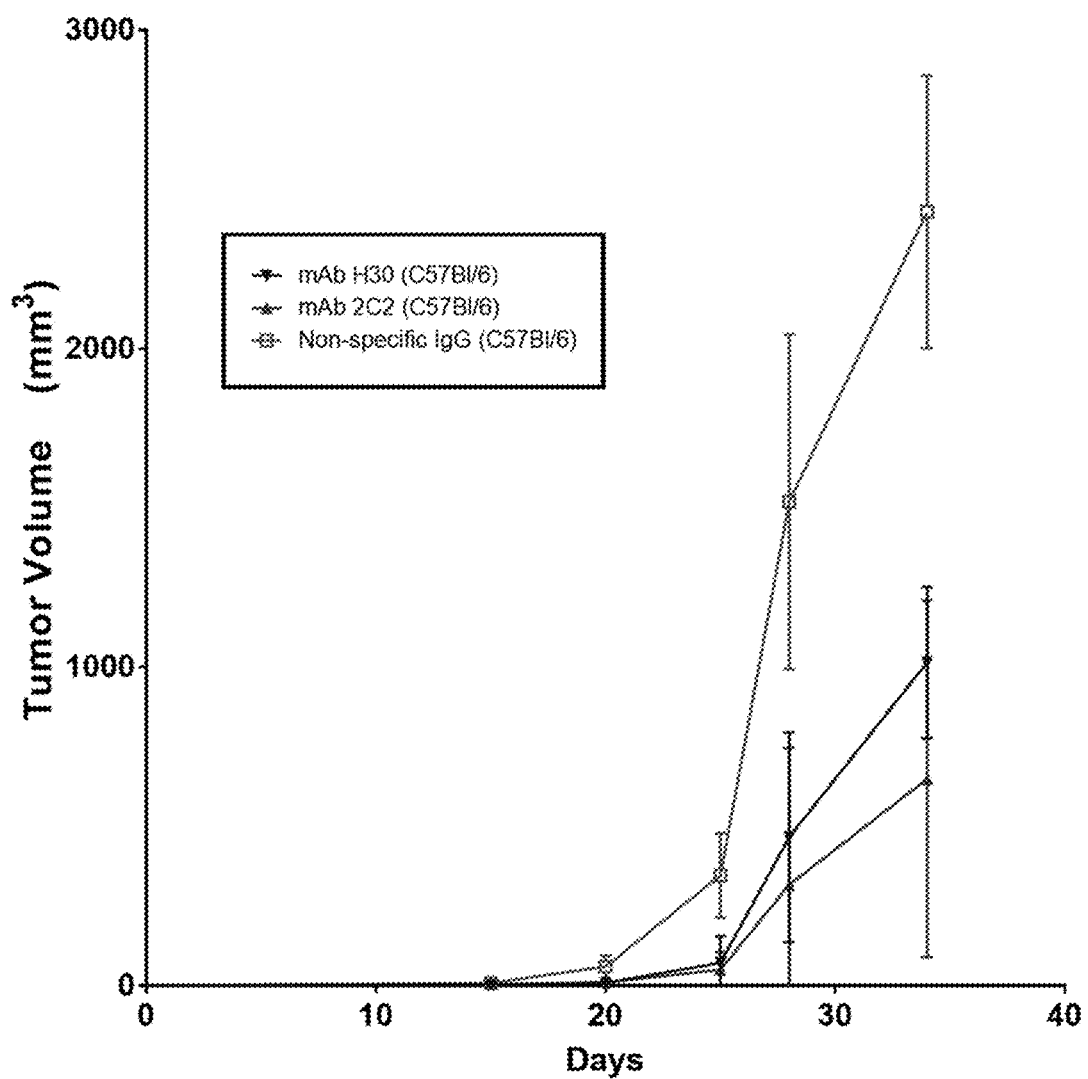
FIG. 7. Representation of effect of two monoclonal antibodies against B16 murine melanoma in C57B1/6 (immunocompetent) mice as a function of time. Tumor volume is shown for groups receiving non-specific IgG, mAb 2C2 and mAb H30.
Figure 8:
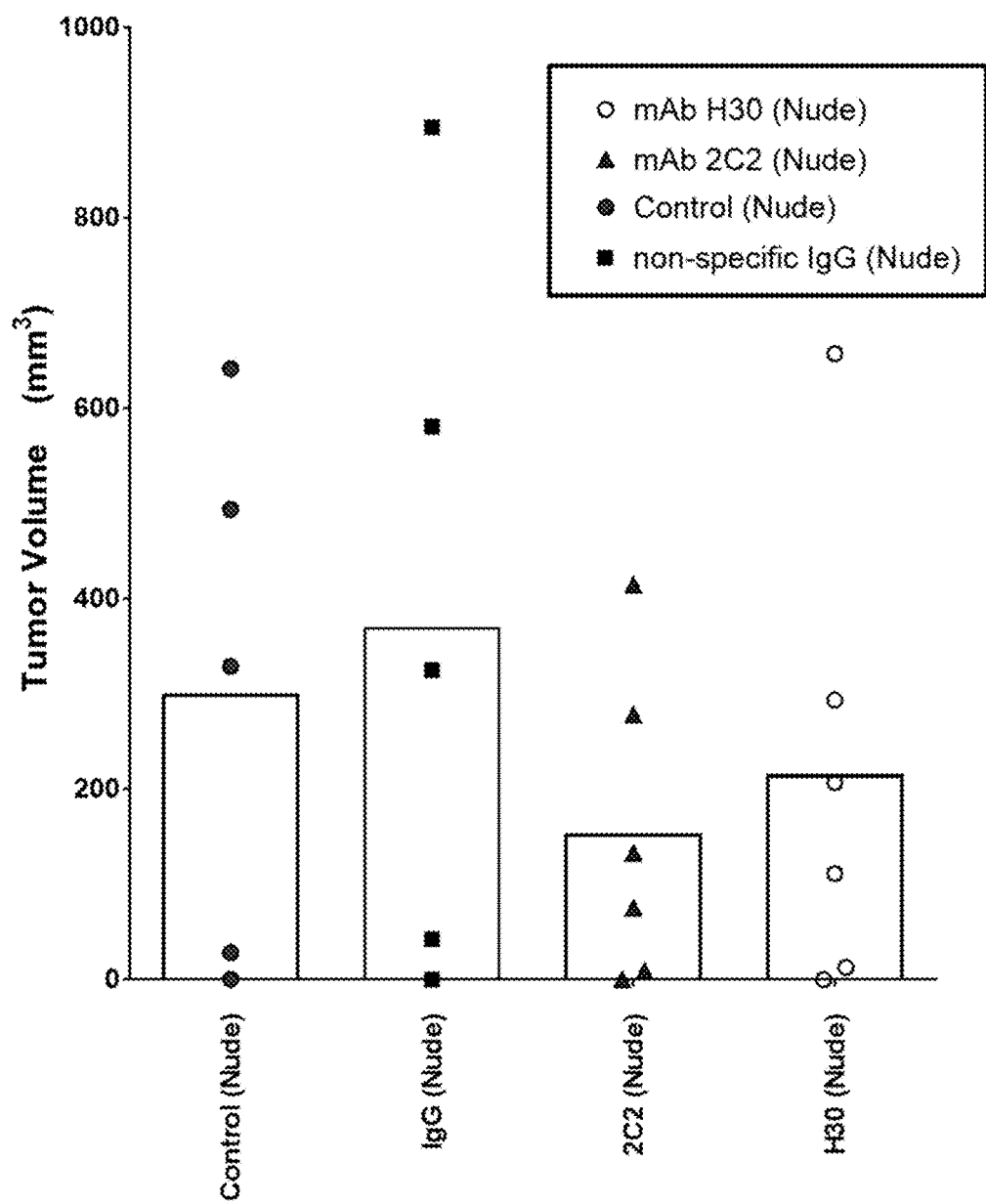
FIG. 8. Representation of effect of two monoclonal antibodies against GL261 murine glioma in Nude (immunocompromised) mice. Tumor volume is shown for control (untreated), groups receiving non-specific IgG, mAb 2C2 and mAb H30. Each point represents one animal.
Figure 9:
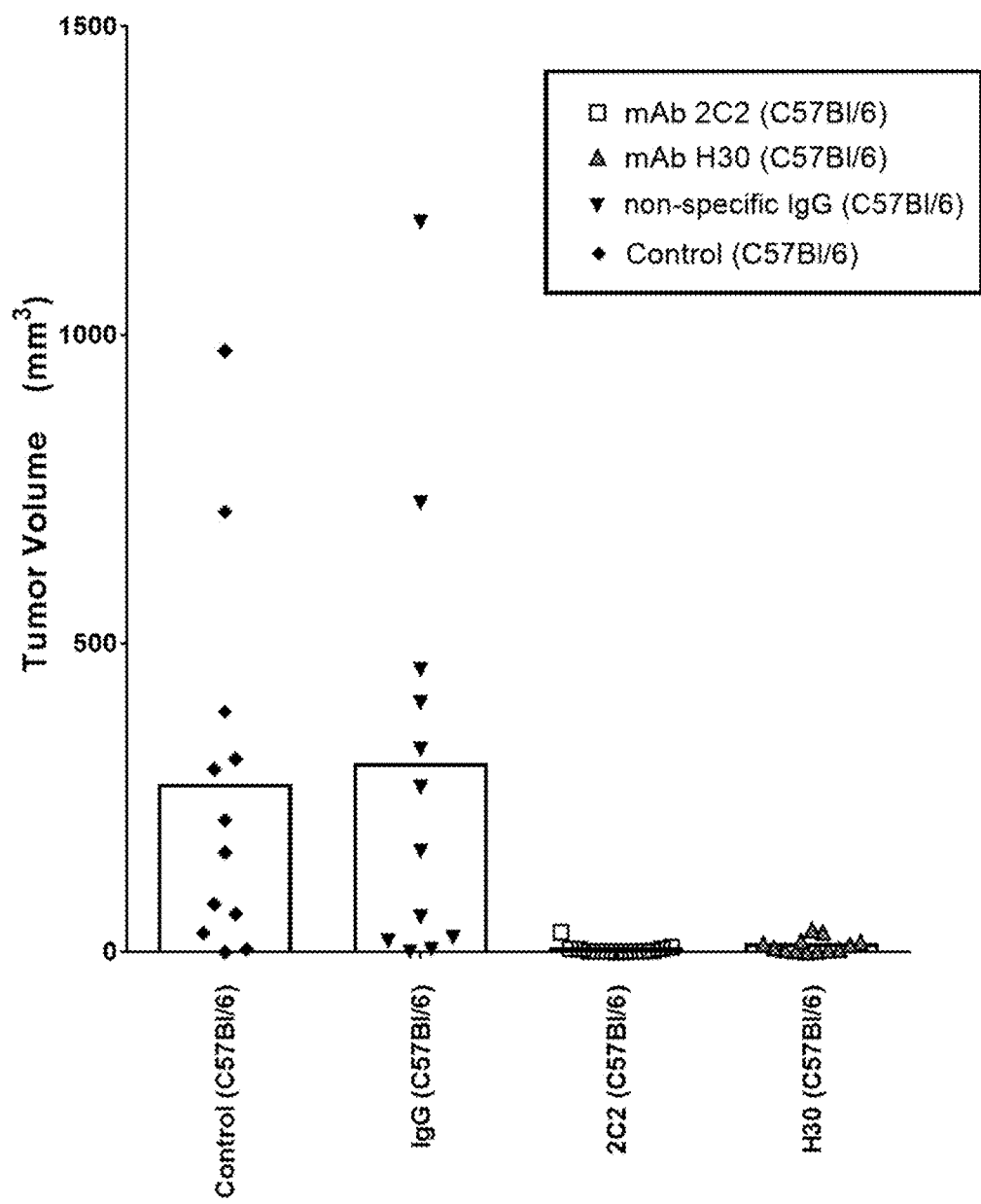
FIG. 9. Representation of effect of two monoclonal antibodies against GL261 murine glioma in C57B1/6 (immunocompetent) mice. Tumor volume is shown for groups receiving control, non-specific IgG, mAb 2C2 and mAb H30. Each point represents one animal.
Figure 10:
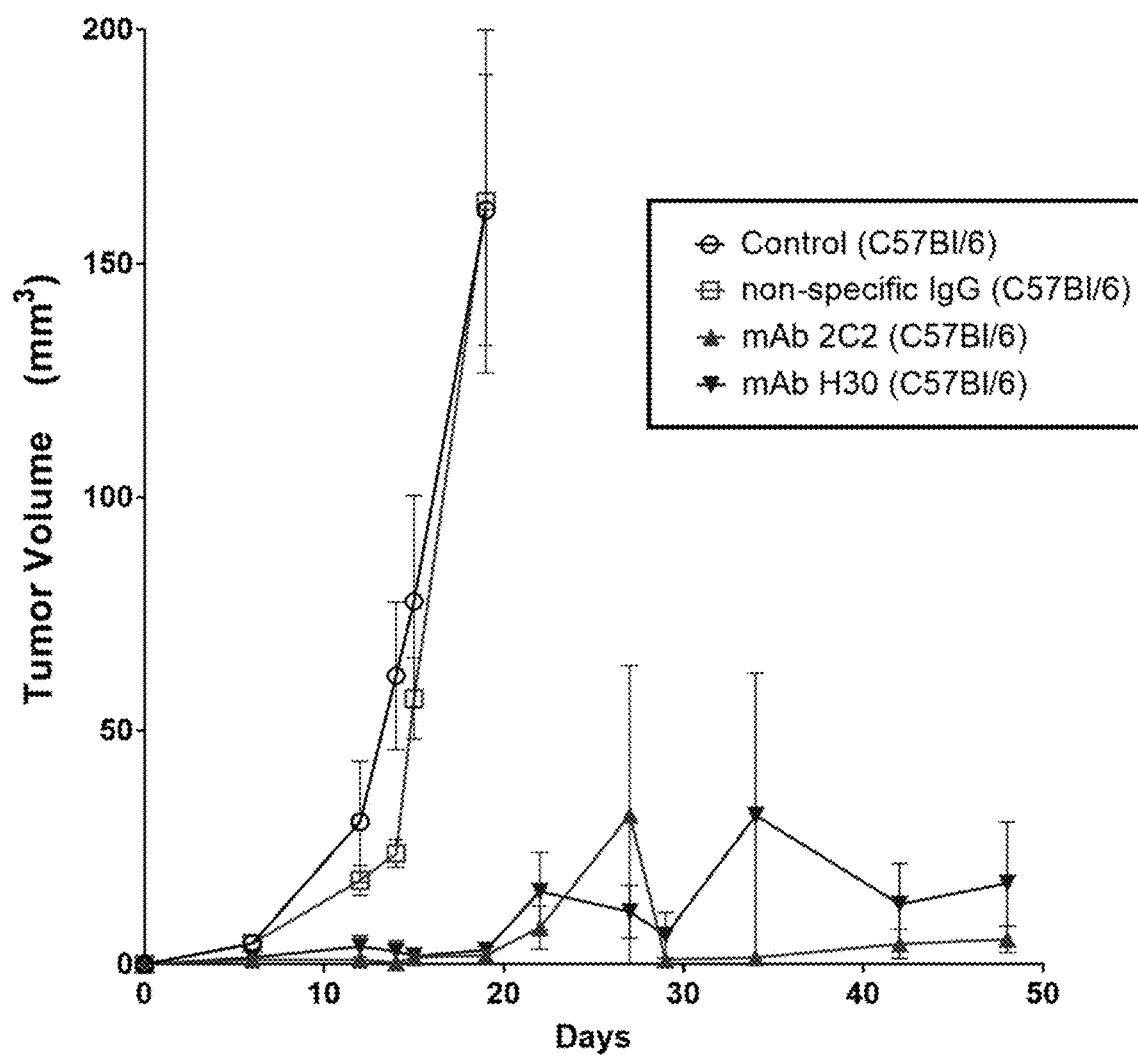
FIG. 10. Representation of effect of two monoclonal antibodies against GL261 murine glioma in C57B1/6 (immuno-competent) mice as a function of time. Tumor volume is shown for groups receiving control, non-specific IgG, mAb 2C2 and mAb H30.
Figure 11:
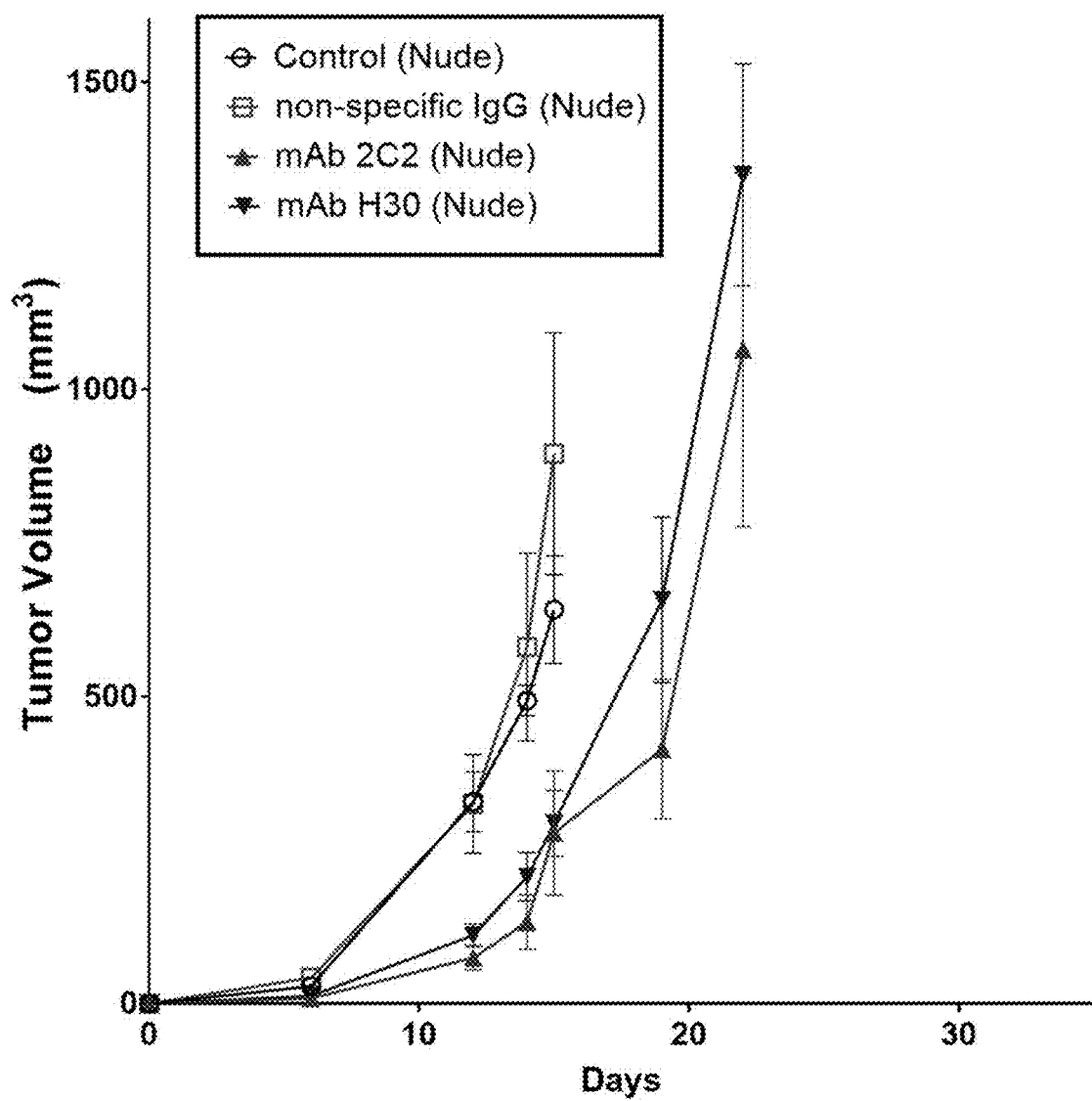
FIG. 11. Representation of effect of two monoclonal antibodies against GL261 murine glioma in Nude (immunocompromised) mice as a function of time. Tumor volume is shown for groups receiving control, non-specific IgG, mAb 2C2 and mAb H30.
Figure 12:
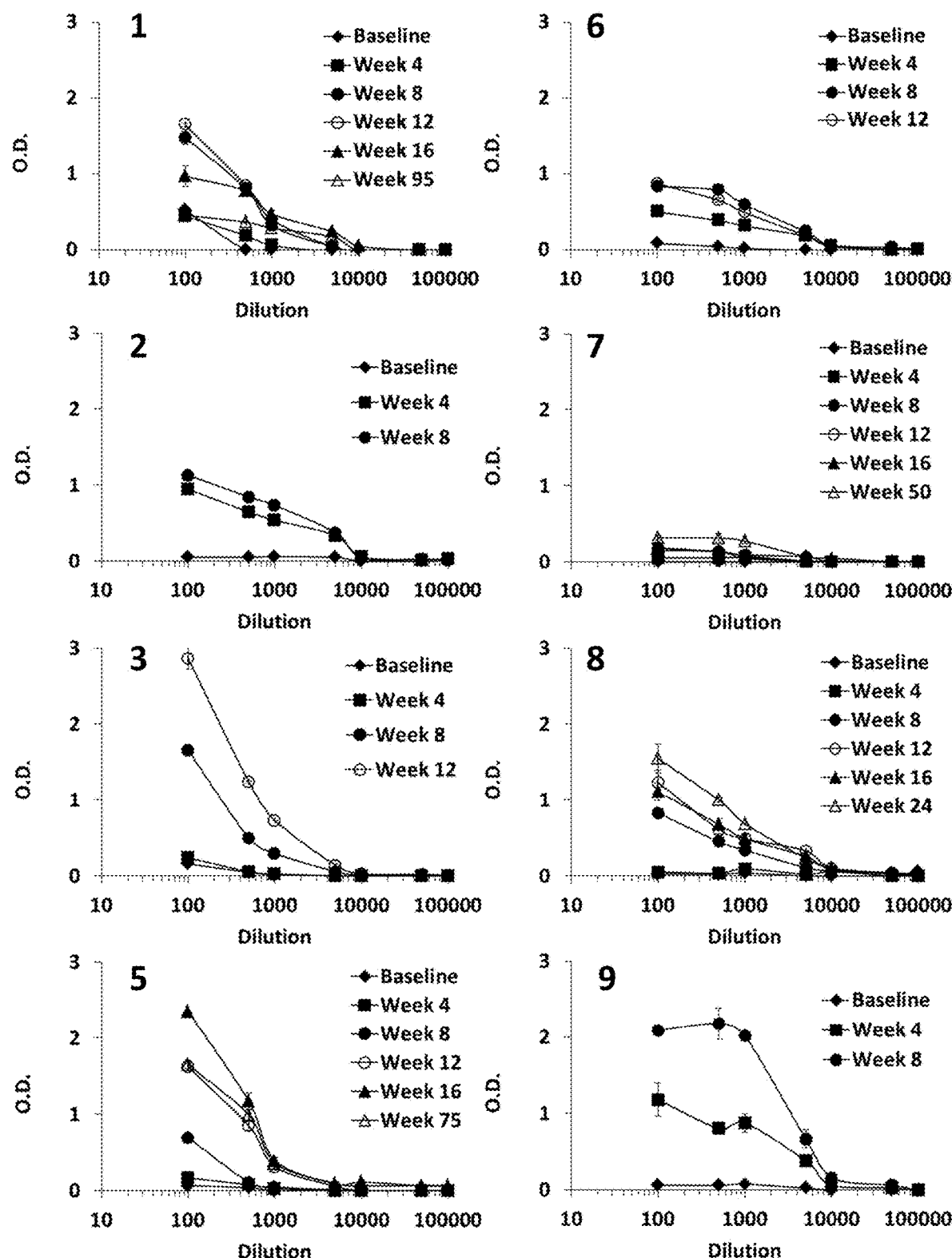
FIG. 12. Representation of generation of total IgG in patients who were administered a survivin vaccine (SEQ ID NO:4). Data is shown for 8 patients. Serum ELISA studies show progressive increase in serum IgG reactivity to wild type survivin peptide (amino acids 53-67 (SEQ ID NO:27).
Figure 13:
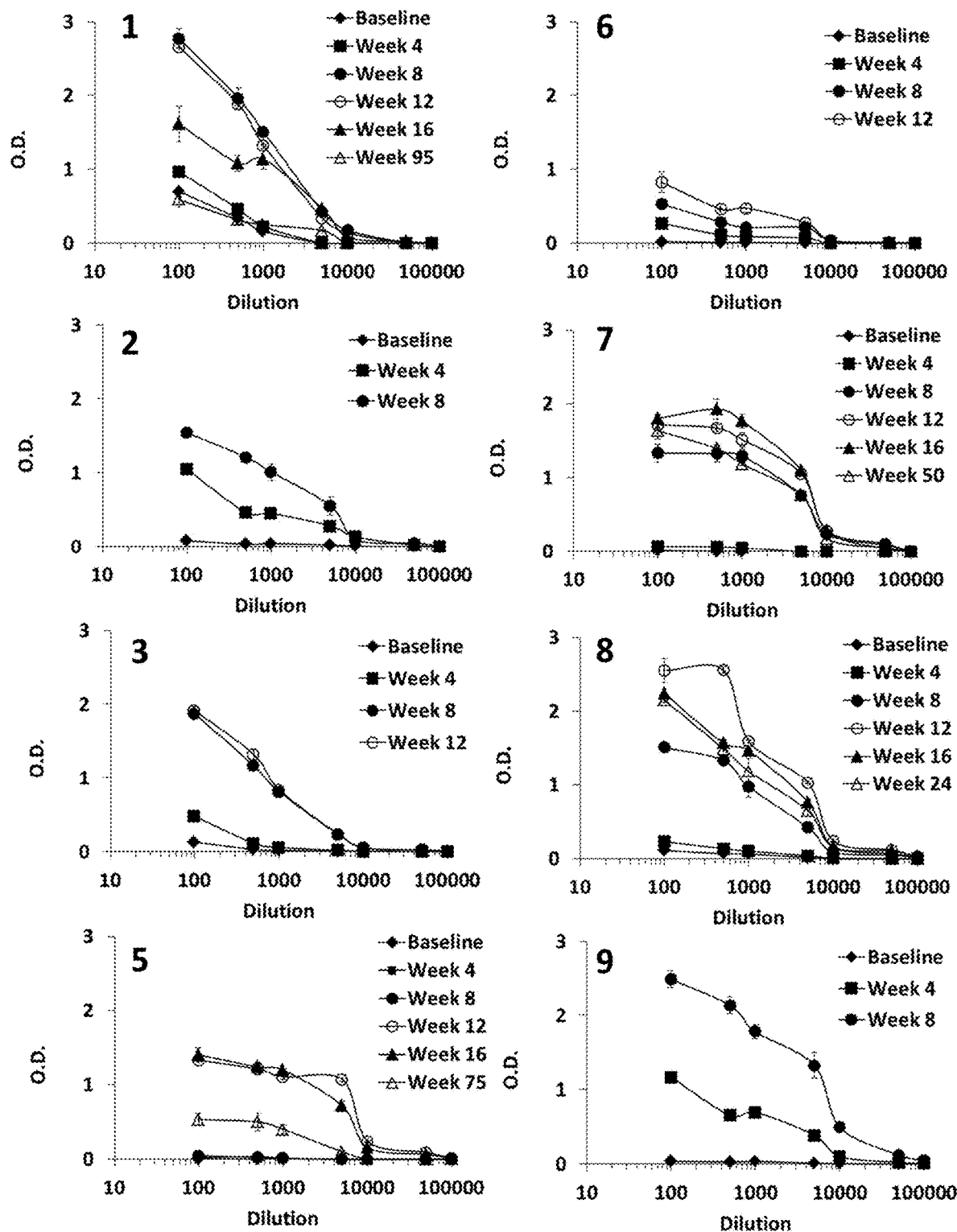
FIG. 13. Representation of generation of survivin specific IgG in patients who were administered a survivin vaccine (SEQ ID NO:4). Data is shown for 8 patients. Serum ELISA studies show progressive increase in serum IgG reactivity to modified survivin peptide (amino acids 53-67/M57—SEQ ID NO:4).

The results of these studies were as follows. As shown in FIG. 1, in intracranial glioma model C57BL/6 mice with GL261 gliomas, who were administered anti-survivin antibody once every 7 days post tumor implantation, mice receiving anti-survivin antibody survived significantly longer than controls. IgG used is normal mouse non-specific IgG. FIG. 2 shows subcutaneous tumor model in C57BL/6 mice with GL261 glioma. Mice were administered the indicated treatments once every 7 days post tumor implantation. Similar to intracranial studies, mice receiving either purified mAb or anti-serum had tumors that were significantly smaller than controls and rivaled the anti-tumor effect observed by the active vaccine itself. FIG. 3 shows subcutaneous tumor model in C57BL/6 mice with GL261 glioma. Mice were administered the indicated treatments once every 7 days post tumor implantation. SurVaxM is the survivin vaccine; anti-survivin sera (antibody) was derived from non-tumor bearing pooled mice receiving active SurVaxM vaccine. Data shows individual tumor growth over 50 days. (n=4 per group)

These data demonstrate that administration of survivin antibodies are effective for reducing tumor volume and prolong survival.

Example 2

This example describes the generation of monoclonal antibodies and the effectiveness of the antibodies for inhibiting tumor growth.

Methods:

Cell lines and culture conditions: GL261 murine glioma cells and B16f1 murine melanoma cell lines are grown on 100-mm tissue culture plates in complete Dulbecco's modified Eagle's medium (DMEM) containing 10% fetal calf serum, 5,000 units penicillin/streptomycin, 50 µM 2-mercaptoethanol, 25 mM HEPES, and 1× non-essential amino acids at 37° C. in 5% $CO_2$ with media changes two to three times per week.

Peptides: Peptide synthesis was performed using Fmoc chemistry and a solid support resin (Genscript, Piscataway, N.J.). Each peptide was stored at −20° C. until use and diluted in DMSO. Antigen sequence 1: DLAQMFFCFKELEGW (SEQ ID NO:4); Antigen sequence 2: DLAQCFFCFKELEGW (SEQ ID NO:27); Immunogen: Peptide (Lot: 614429-1)-KLH conjugate.

Immunization of mice for antibody production: Ten mice were used per round of antibody production. 5 Balb/c mice and 5 C57Bl/6 mice were used to produce anti-serum reactive against antigen 1 (SVN53-67/M57). Mice were immunized with Immunogen: Peptide-KLH conjugate (SVN53-67/M57-KLH). Serum samples were obtained after 4 rounds of immunization. Upon confirmation of survivin reactive anti-serum through indirect ELISA analysis, positive-testing mice were selected for hybridoma production. Several hybridoma cell lines were produced with cells from each reactive mouse fused to SP2/0 myeloma cells. Of these cell lines 2 subclones were further isolated and characterized.

Indirect ELISA for antibody reactivity: 96 well ELISA plates were coated with 1 µg/ml, 100 µl/well of either Coating Antigens: A: (SVN53-67/M57) DLAQMFFCFKELEGW (SEQ ID NO:4) or B: (wild type SVN53-67) DLAQCFFCFKELEGW (SEQ ID NO:27) in Phosphate Buffered Saline, pH 7.4. Murine anti-serum or hybridoma cell culture supernatant was applied 100 ul/well to coated plates and incubated. Secondary Antibody: Peroxidase-AffiniPure Goat Anti-Mouse IgG, Fcγ was then added followed with standard detection.

Hybridoma sequencing: Total RNA was isolated from the hybridoma cells following the technical manual of TRIzol® Reagent (Ambion, Cat. No.: 15596-026). The total RNA was analyzed by agarose gel electrophoresis. Total RNA was reverse transcribed into cDNA using isotype-specific antisense primers or universal primers following the technical manual of PrimeScript™ 1st Strand cDNA Synthesis Kit (Takara, Cat. No.: 6110A). The antibody fragments of VH and VL were amplified according to the standard operating procedure of RACE of GenScript. Amplified antibody fragments were separately cloned into a standard cloning vector using standard molecular cloning procedures. Colony PCR screening was performed to identify clones with inserts of correct sizes. No less than five single colonies with inserts of correct sizes were sequenced for each antibody fragment. Five single colonies with correct VH and VL insert sizes were sent for sequencing. The VH and VL genes of five different clones were found nearly identical. The consensus sequence is believed to be the sequence of the antibody produced.

Patient Serum Antibody Measurements: Patient serum was collected and stored at −80° C. Serial dilutions of clarified serum were applied to unconjugated survivin peptide, free KLH and random peptide (20 µg/ml, 1 µg/well) on pre-coated ELISA plates (Flat Bottom, Nunc) in triplicate. Samples were incubated at 4° C. overnight and washed (PBS, 1% BSA). HRP conjugated anti-human IgG detection antibody (Bio-Rad) was added for 1 hour at 25° C. Plates were washed 4 times and TMB colorimetric solution (Biolegend) was added at room temperature and developed for 15 minutes and read on a Bio-Rad automated plate reader at 450 nm.

Immunization of mice for tumor growth studies: Proof of principle studies in mice were performed with 100 µl of anti-SVN53-67/M57 hybridoma supernatant or 10 µg of purified monoclonal antibody. Mice were first implanted with murine GL261 glioma cells or B16f1 murine melanoma cells either intracranially or subcutaneously. At four days post tumor implantation mice received i.p. injections of antibody repeated once weekly for a maximum of 5 weeks and followed for tumor growth.

Intracerebral GL261 tumor cell injection and survival analysis: Male C57BL/6 mice (Charles River, Horsham, Pa.) were anesthetized with gas isoflurane and fixed in a stereotactic head frame (David Kopf Instruments, Tujunga, Calif.). A midline scalp incision was made and the bregma was identified. Stereotactic coordinates were measured (2.0 mm lateral, and 1.2 mm anterior to the bregma) for implantation of cells into the deep frontal white matter. A burr hole was drilled at this point and $1\times10^5$ GL261 cells suspended in 2.5 µl of DMEM were injected through a Hamilton syringe with a fixed, 25-gauge needle at a depth of 3.0 mm relative to the dura mater. Injections were performed at 1 µl/min. The needle was withdrawn and the incision sutured. Kaplan-Meier survival plots were drawn and median survival times were determined for all groups. n=8 mice per group.

Subcutaneous tumor growth studies: A suspension of $2\times10^7$ G1261 cells or $1\times10^6$ B16f1 cells in 100 µl of PBS was injected into the shaved right flank subcutaneous skin of male C57B1/6 (immunocompetent) mice (Charles River, Horsham, Pa.) as well as Nude (immunocompromised) NCr-nu/nu mice (Charles River, Horsham, Pa.). Tumor growth was measured daily with calipers, and volumes were calculated according to the formula $V=(a\cdot(b^2))/2$, where V is volume and a and b are perpendicular diameters of the tumor. Data is presented as tumor growth over time as well as comparative mean tumor volumes. n=4, 5 or 10 mice per group in various studies presented as indicated.

Results:

A modified survivin peptide of SEQ ID NO: 4 was used to generate hybridomas. Ten mice were administered 15 µg/ml peptide vaccine comprising the peptide of SEQ ID NO:4. Out of these 9 mice developed anti-survivin titers. Several hybridoma lines were generated which produced antibodies that were reactive against peptide of SEQ ID NO:4 and a survivin peptide DLAQCFFCFKELEGW (SEQ ID NO:27) in which the sequence is identical to a portion of human survivin. Out of the hybridomas, two in particular were selected for further characterization. These are termed as 2C2 and the 30H3. From these hybridomas, one clone each was further characterized. These are termed as 2C2E7 and 30H3D2 respectively. 2C2E7 was found to have the isotype IgG2b and 30H3D2 was found to have the isotype IgG1. Therefore, A few single colonies with correct heavy and light chain variable region insert sizes were sequenced. The sequences were found to be nearly identical and consensus sequences were generated. Consensus amino acid sequence for the heavy and light chain variable regions from the mAb 2C2E7 are provided in SEQ ID NOs:19 and 20 respectively. Consensus amino acid sequence for the heavy and light chain variable regions from the mAb 30H3D2 are provided in SEQ ID NOs:21 and 22 respectively. The corresponding nucleotide sequences for the amino acid sequences of SEQ ID NOs:19, 20, 21 and 22 are provided in SEQ ID NOs:23, 24, 25 and 26 respectively.

The consensus amino acid sequence for heavy chain variable region from antibody 2C2E7 is shown below:

```
                                             (SEQ ID NO: 19)
MGWLWNLLFLMAAAQSAQAQIQLVQSGPELKKPGETVKISCKASGYTFTT
YGMSWVKQAPGRGLKWMGWINPYSGVPTYAVDFKGRFAFSLETSASTAYL
QINNLKNEDTATYFCARGGRRGDFGYWGQGTTLTVSS.
```

The consensus amino acid sequence for light chain variable region from antibody 2C2E7 is shown below:

```
                                             (SEQ ID NO: 20)
MDFQVQIFSFLLISASVILSSGQIGLTQSPAIMSASPGEKVTMTCSASSS
ISYMHWYQQKPGTSPKTWIYDTSKLASGVPARFSGSGSGTSYSLTISSME
AEDAATYYCHQRSSHHTFGGGTKLEIK.
```

The consensus amino acid sequence for heavy chain variable region from antibody 30H3D2 is shown below:

```
                                             (SEQ ID NO: 21)
MNFGLSLIFLALILKGVQCEVQLVESGGDLVKPGGSLKLSCAASGFTFSS
YGMSWVRLTPDKRLEWVATISSGGSHTYYPDSVRGRFTISRDNAKNTLYL
QMSSLKSEDTAMYYCARHPIYYYISSYAMDYWGQGTSVTVSS.
```

The consensus amino acid sequence for light chain variable region from antibody 30H3D2 is shown below:

```
                                             (SEQ ID NO: 22)
MKLPVRLLVLMFWIPASSSDVVMTQTPLSLPVSLGDQASISCRSSQSLVH
STGNTYLHWYLQKPGQSPKLLIYKVSNRFSGVPDRFGGSGSGTDFTLKIS
RVEAEDLGVYFCSQSTHVPPTFGGGTKLEIK.
```

A nucleotide sequence encoding the amino acids of heavy chain variable domain set forth in SEQ ID NO:19 of mAb 2C2E7 is shown below:

```
                                             (SEQ ID NO: 23)
ATGGGTTGGCTGTGGAACTTGCTATTCCTGATGGCAGCTGCCCAAAGTGC

CCAAGCACAGATCCAGTTGGTACAATCTGGACCTGAGCTGAAGAAGCCTG

GAGAGACAGTCAAGATCTCCTGCAAGGCTTCTGGGTATACCTTCACAACC

TATGGAATGAGCTGGGTGAAACAGGCTCCAGGAAGGGGTTTAAAGTGGAT

GGGCTGGATAAACCCCTACTCTGGAGTGCCAACATATGCTGTTGACTTCA

AGGGACGGTTTGCCTTCTCTTTGGAAACCTCTGCCAGCACTGCCTATTTG

CAGATCAACAACCTCAAAAATGAGGACACGGCTACATATTTCTGTGCAAG

AGGAGGGCGGAGGGGGACTTTGGCTACTGGGGCCAAGGCACCACTCTCA

CAGTCTCCTCA.
```

A nucleotide sequence encoding the amino acids of light chain variable domain set forth in SEQ ID NO:20 of mAb 2C2E7 is shown below:

(SEQ ID NO: 24)
ATGGATTTTCAGGTGCAGATTTTCAGCTTCCTGCTAATCAGTGCCTCAGT

CATACTGTCCAGCGGACAAATTGGTCTCACCCAGTCTCCAGCAATCATGT

CTGCATCTCCAGGGGAGAAGGTCACCATGACCTGCAGTGCCAGCTCAAGT

ATAAGTTACATGCATTGGTACCAGCAGAAGCCAGGCACCTCCCCCAAAAC

ATGGATTTATGACACATCCAAACTGGCTTCTGGAGTCCCTGCTCGCTTCA

GTGGCAGTGGGTCTGGGACCTCTTATTCTCTCACAATCAGCAGCATGGAG

GCTGAAGATGCTGCCACTTATTACTGCCATCAGCGGAGTAGTCACCACAC

GTTCGGAGGGGGACCAAGCTGGAAATAAAA.

A nucleotide sequence encoding the amino acids of heavy chain variable domain set forth in SEQ ID NO:21 of mAb 30H3D2 is shown below:

(SEQ ID NO: 25)
ATGAACTTCGGGCTCAGCTTGATTTTCCTTGCCCTTATTTTAAAAGGTGT

CCAGTGTGAGGTGCAGCTGGTGGAGTCTGGGGGAGACTTAGTGAAGCCTG

GAGGGTCCCTGAAACTCTCCTGTGCAGCCTCTGGATTCACTTTCAGTAGC

TATGGCATGTCTTGGGTTCGCCTGACTCCAGACAAGAGGCTGGAGTGGGT

CGCAACCATTAGCAGTGGTGGTAGTCACACCTACTATCCAGACAGTGTGA

GGGGGCGATTCACCATCTCCAGAGACAATGCCAAGAACACCCTGTACCTG

CAAATGAGCAGTCTGAAGTCTGAGGACACAGCCATGTATTACTGTGCAAG

ACACCCAATTTATTACTACATTAGTAGCTATGCTATGGACTACTGGGGTC

AAGGAACCTCAGTCACCGTCTCCTCA.

A nucleotide sequence encoding the amino acids of light chain variable domain set forth in SEQ ID NO:22 of mAb 30H3D2 is shown below:

(SEQ ID NO: 26)
ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTAGTCAGAGCCTTGTACAC

AGTACTGGAAACACCTATTTACATTGGTACCTGCAGAAGCCAGGCCAGTC

TCCAAAGCTCCTGATCTACAAAGTTTCCAACCGATTTTCTGGGGTCCCAG

ACAGGTTCGGTGGCAGTGGATCAGGGACAGATTTCACACTCAAGATCAGC

AGAGTGGAGGCTGAGGATCTGGGAGTTTATTTCTGCTCTCAAAGTACACA

TGTTCCTCCGACGTTCGGTGGAGGCACCAAGCTGGAAATCAAA.

The antibodies were tested for binding against the peptide used for immunizing the animals (SEQ ID NO:4), and against a sequence from human survivin (SEQ ID NO:27). 15 ng/ml antibody concentration of 2C2E7 was sufficient to bind the modified survivin peptide of SEQ ID NO:4 at an OD of 1.019 and wild type survivin peptide of SEQ ID NO:27 at an OD of 0.891. The titer of 2C2E7 at its highest dilution with signal to blank ratio of >2:1 is 1:512,000 consistent with that expected for a high affinity antibody. Further, 31 ng/ml antibody concentration of 30H3D2 was sufficient to bind the modified survivin peptide of SEQ ID NO:4 at an OD of 1.021 and wild type survivin peptide of SEQ ID NO:27 at an OD of 0.874. The titer of 30H3 at its highest dilution with signal to blank ratio of >2:1 is 1:512,000 is consistent with that expected for a high affinity antibody.

The antibodies were then used in animal models to determine the effect of growth of tumors. The animal models were same as used in Example 1. The results are shown in FIGS. 4 to 11. Studies of 2C2 and H30 anti-survivin antibodies were performed in subcutaneous murine tumor models. Mice were allowed to establish an implantable tumor after which they began treatment with 2C2, H30 or non-specific IgG every 5-7 days for a 30 day period. Two host mouse strains were used, NCr-nu/nu (nude) in FIGS. 4, 6, 8, 10 and C57B1/6 mice in FIGS. 5, 7, 9, 11. Nude mice represent an immunocompromised model in which activity of antibodies would be expected to specifically depend on direct antibody binding to target without immune system support. C57B1/6 mice represent an immunocompetent model where antibodies may benefit from the additional engagement of immunological support mechanisms such as Macrophages, Dendritic cells and T cells. B16 melanoma FIGS. 4-7 and GL261 glioma cells FIGS. 8-11 were shown to be growth inhibited in the C57B1/6 (immunocompetent) model (FIGS. 5, 7) and to a lesser extent also growth inhibited in the nude (immunocompromised) model (FIGS. 4, 6) when treated with 2C2 or H30 antibodies. This observation shows a strong immune-mediated antibody-dependent response in C57B1/6 mice (FIGS. 5, 7, 9, 11) that is not completely abrogated by the lack of immune support in Nude mice (FIGS. 4, 6, 8, 10). In immunocompromised models (FIGS. 4, 6, 8, 10) the persistence of antibody-dependent growth inhibition strongly suggests an added immune system independent or direct growth inhibitory component of antibody by itself. Glioma patients enrolled in a Phase I clinical trial at Roswell Park Cancer Institute of SurVaxM (SVN53-67/M57-KLH) SEQ. ID NO:4 (FDA approved/I171010) were observed to produce an unexpected antibody response to the SurVaxM peptide during their clinical trial protocol period. Eight patients shown here produce a reactive anti-sera that is cross reactive to both wild type survivin peptide comprised of amino acids of SEQ ID NO:27 as well as the modified survivin peptide comprised of amino acids of SEQ ID NO:4 which is also contained in the 15 amino acid immunizing peptide sequence. These antibodies can be used for therapeutic purposes.

Although the present disclosure has been described using specific embodiments and examples, routine modifications will be apparent to those skilled in the art and such modifications are intended to be within the scope of the disclosure and the claims.

The invention claimed is:

1. A chimeric antigen receptor (CAR) comprising an antibody that binds to Survivin, wherein the antibody comprises a heavy chain variable region and a light chain variable region, wherein:
   a) the heavy chain variable region comprises a VH CDR1 comprising the sequence of SEQ ID NO:7, a VH CDR2 comprising the sequence of SEQ ID NO:8, and a VH CDR3 comprising the sequence of SEQ ID NO:9, and the light chain variable region comprises a VL CDR1 comprising the sequence of SEQ ID NO:10, a VL CDR2 comprising the sequence of SEQ ID NO:11, and a VL CDR3 comprising the sequence of SEQ ID NO:12; or
   b) the heavy chain variable region comprises a VH CDR1 comprising the sequence of SEQ ID NO:13, a VH CDR2 comprising the sequence of SEQ ID NO:14, and a VH CDR3 comprising the sequence of SEQ ID NO:15, and the light chain variable region comprises a VL CDR1 comprising the sequence of SEQ ID NO:16, a VL CDR2 comprising the sequence of SEQ ID NO:17, and a VL CDR3 comprising the sequence of SEQ ID NO:18.

2. The CAR of claim 1, wherein the antibody is a scFv.

3. An isolated transformed T cell which comprises the CAR of claim 1.

4. An isolated transformed T cell into which has been introduced polynucleotide sequences encoding a heavy chain variable region and a light chain variable region of an antibody that binds to Survivin, wherein the heavy chain variable region comprises a VH CDR1 comprising the sequence of SEQ ID NO: 7, a VH CDR2 comprising the sequence of SEQ ID NO: 8, and a VH CDR3 comprising the sequence of SEQ ID NO: 9, and the light chain variable region comprises a VL CDR1 comprising the sequence of SEQ ID NO: 10, a VL CDR2 comprising the sequence of SEQ ID NO: 11, and a VL CDR3 comprising the sequence of SEQ ID NO: 12.

5. An isolated transformed T cell into which has been introduced polynucleotide sequences encoding heavy chain variable region and a light chain variable region of an antibody that binds to Survivin, wherein the heavy chain variable region comprises a VH CDR1 comprising the sequence of SEQ ID NO: 13, a VH CDR2 comprising the sequence of SEQ ID NO: 14, and a VH CDR3 comprising the sequence of SEQ ID NO: 15, and the light chain variable region comprises a VL CDR1 comprising the sequence of SEQ ID NO: 16, a VL CDR2 comprising the sequence of SEQ ID NO: 17, and a VL CDR3 comprising the sequence of SEQ ID NO: 18.

* * * * *